(12) United States Patent
Okada et al.

(10) Patent No.: US 7,662,089 B2
(45) Date of Patent: Feb. 16, 2010

(54) ENDOSCOPE SUITABLE TO BODY CAVITY

(75) Inventors: Yuta Okada, Hachioji (JP); Yoshio Onuki, Hino (JP); Hideki Shimonaka, Hachioji (JP); Koichi Kawashima, Hachioji (JP)

(73) Assignee: Olympus Corporation, Tokyo (JP)

( * ) Notice: Subject to any disclaimer, the term of this patent is extended or adjusted under 35 U.S.C. 154(b) by 259 days.

(21) Appl. No.: 10/914,730

(22) Filed: Aug. 9, 2004

(65) Prior Publication Data

US 2005/0090709 A1  Apr. 28, 2005

Related U.S. Application Data

(60) Provisional application No. 60/505,147, filed on Sep. 23, 2003.

(51) Int. Cl.
*A61B 1/00* (2006.01)

(52) U.S. Cl. ........................ 600/113; 600/104

(58) Field of Classification Search ......... 600/172–175, 600/182, 107, 114, 113, 153, 104, 121–123, 600/165, 106, 164, 166, 170, 128–131
See application file for complete search history.

(56) References Cited

U.S. PATENT DOCUMENTS

| | | | | |
|---|---|---|---|---|
| 4,375,818 A * | 3/1983 | Suwaki et al. | ............... | 600/463 |
| 4,586,491 A * | 5/1986 | Carpenter | ................... | 600/113 |
| 4,846,154 A * | 7/1989 | MacAnally et al. | ......... | 600/171 |
| 4,947,828 A * | 8/1990 | Carpenter et al. | ............ | 600/113 |
| 5,328,365 A * | 7/1994 | Jacoby | .......................... | 433/29 |
| 5,547,455 A * | 8/1996 | McKenna et al. | ............ | 600/113 |
| 5,940,126 A * | 8/1999 | Kimura | ....................... | 348/294 |
| 5,976,076 A * | 11/1999 | Kolff et al. | ................... | 600/166 |
| 6,066,090 A * | 5/2000 | Yoon | ........................... | 600/113 |
| 6,261,226 B1 * | 7/2001 | McKenna et al. | ........... | 600/109 |
| 6,547,723 B1 * | 4/2003 | Ouchi | ........................ | 600/146 |
| 6,997,871 B2 * | 2/2006 | Sonnenschein et al. | ..... | 600/173 |
| 2003/0163029 A1 * | 8/2003 | Sonnenschein et al. | ..... | 600/160 |
| 2004/0204629 A1 * | 10/2004 | Knapp | ........................ | 600/156 |
| 2004/0254422 A1 * | 12/2004 | Singh | ......................... | 600/160 |

\* cited by examiner

*Primary Examiner*—John P Leubecker
*Assistant Examiner*—Victoria W Chen
(74) *Attorney, Agent, or Firm*—Scully, Scott, Murphy & Presser, P.C.

(57) ABSTRACT

An endoscope for treatment suitable to the treatment in a body cavity comprises an elongated soft observing optical unit having at least an observing optical system; and a unit inserting tool having a unit inserting channel in which the observing optical unit is inserted and a treatment tool inserting channel in which a treatment tool is inserted. The unit inserting channel of the unit inserting tool has a branching portion at which the unit inserting channel is branched into a first inserting channel and a second inserting channel. An observing window which is arranged at the end opening of the first inserting channel is provided in a surface at the distal-end and an observing window which is arranged at the end opening of the second inserting channel is provided in a surface at the halfway portion. The unit inserting tool comprises an optical unit guiding port for guiding the observing optical unit and at least one treatment tool lead-in port in which a treatment tool is inserted at the proximal end portion and a treatment tool lead-out port which is communicated with the treatment tool inserting channel that extends from the treatment tool lead-in port at least in one of the surface at the distal-end and the surface at the halfway portion.

10 Claims, 20 Drawing Sheets

ENDOSCOPE SUITABLE TO BODY CAVITY

CROSS-REFERENCE TO RELATED APPLICATION

This application claims the benefit of priority from U.S. provisional application Ser. No. 60/505,147 filed on Sep. 23, 2003.

BACKGROUND OF THE INVENTION

1. Field of the Invention

The present invention relates to an endoscope which performs the treatment by using a treatment tool while observing the body cavity with the endoscope inserted therein.

2. Description of the Related Art

An endoscope comprises a treatment tool inserting channel. Recently, an operator observes an observation image captured by an observing optical system provided for the endoscope and simultaneously performs various treatments by inserting the treatment tool via the treatment tool inserting channel and guiding the treatment tool from a treatment tool lead-out port.

Preferably, the treatment tool lead-out ports of the treatment tool inserting channels are arranged at the best positions corresponding to the treatment, in the treatment with a plurality of treatment tools. Specifically, one treatment tool lead-out port is arranged at the halfway portion of an inserting portion, and another treatment tool lead-out port is arranged to the distal end portion. Thus, the body tissue is picked up by gripping forceps after being guided from the distal end portion, and the picked-up body tissue is incised by a knife guided from the halfway portion.

When the endoscope is orally inserted in the body cavity and the ligation is performed, a distal-end hood having a needle, a thread, and thread removing means is attached to the distal end portion of the endoscope. A pricking needle is pricked to the body tissue for the purpose of the ligation treatment.

SUMMARY OF THE INVENTION

An endoscope for treatment suitable to the treatment in a body cavity comprises an elongated soft observing optical unit having at least an observing optical system; and a unit inserting tool having a unit inserting channel in which the observing optical unit is inserted and a treatment tool inserting channel in which a treatment tool is inserted. The unit inserting channel of the unit inserting tool has a branching portion at which the unit inserting channel is branched into a first inserting channel and a second inserting channel. An observing window which is arranged at the end opening of the first inserting channel is provided in a surface at the distal end and an observing window which is arranged at the end opening of the second inserting channel is provided in a surface at the halfway portion. The unit inserting tool comprises an optical unit guiding port for guiding the observing optical unit and at least one treatment tool lead-in port in which a treatment tool is inserted at the proximal end portion and a treatment tool lead-out port which is communicated with the treatment tool inserting channel that extends from the treatment tool lead-in port at least in one of the surface at the distal end and the surface at the halfway portion.

The above and other objects, features, and advantages of the invention will become more clearly understood from the following description referring to the accompanying drawings.

DETAILED DESCRIPTION OF THE PREFERRED EMBODIMENTS

Hereinbelow, a description is given of embodiments of the present invention with reference to the drawings.

The first embodiment will be described with reference to FIGS. 1 to 6.

Figure 1:
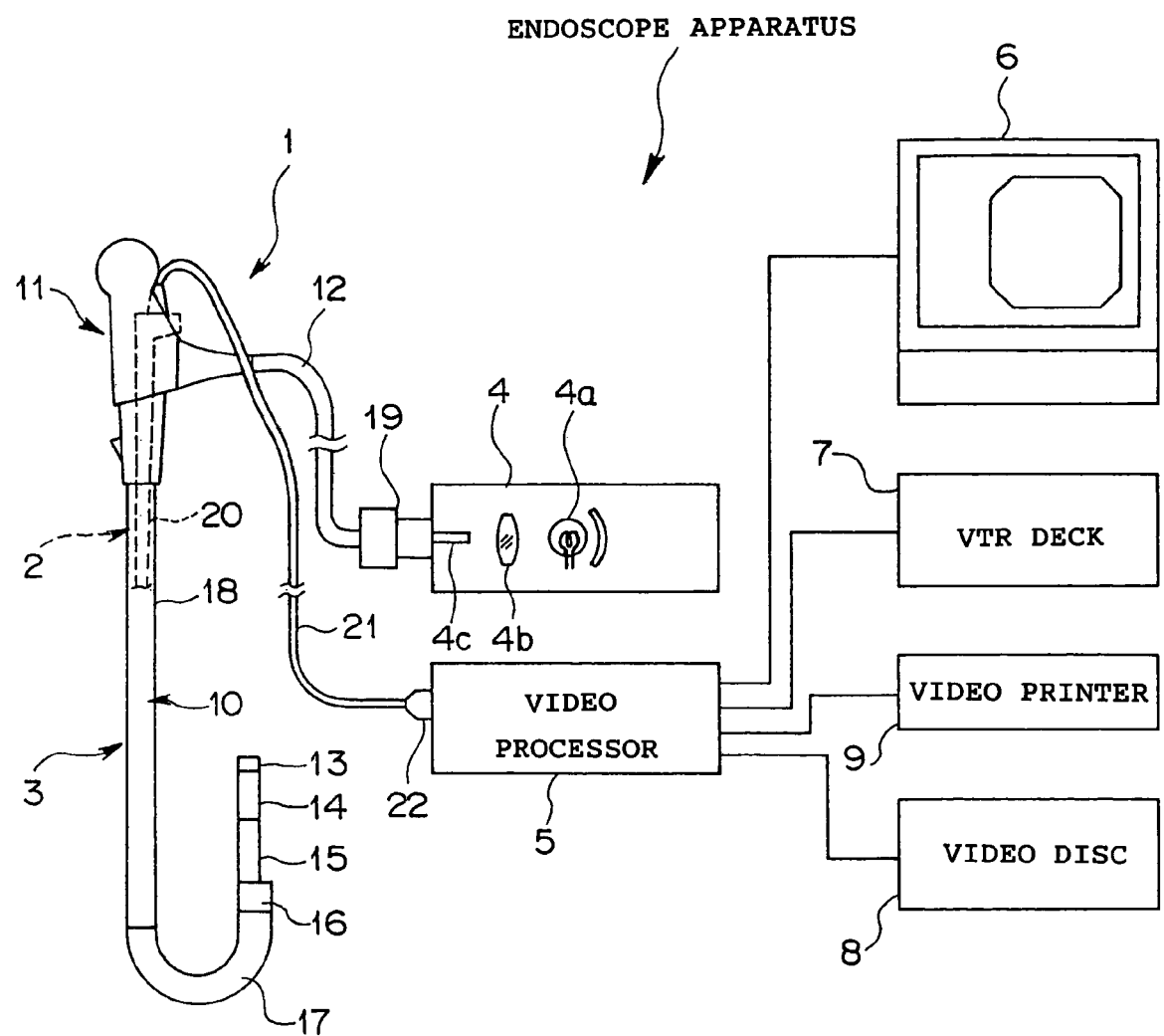
FIG. 1 is a diagram for explaining the structure of an endoscope for treatment having an observing unit and a unit inserting tool and an endoscope apparatus for treatment having the endoscope for treatment.

Referring to FIG. 1, an endoscope apparatus for treatment (hereinafter, abbreviated to an endoscope apparatus) mainly comprises: an endoscope for treatment (hereinafter, abbreviated to an endoscope) 1; a light source device 4; a video processor 5; a monitor 6; a VTR deck 7; a video disc 8; and a video printer 9. The endoscope 1 comprises an observing optical unit (hereinafter, abbreviated to an observing unit) 2; and a unit inserting tool 3.

The observing unit 2 comprises an elongated unit inserting portion 20 with the flexibility. The unit inserting portion 20 is inserted and is arranged in a unit inserting channel, which will be described later, arranged in a unit inserting portion (hereinafter, abbreviated to an inserting portion) 10 forming the unit inserting tool 3. A scope cable 21 is extended from a proximal end portion of the unit inserting portion 20. A video connector 22 is detachably connected to the video processor 5, and is arranged to the proximal end portion of the scope cable 21.

The unit inserting tool 3 comprises the inserting portion 10 with the flexibility; an operating portion 11 functioning as a grip portion; and a universal cord 12. The inserting portion 10 is composed of a distal-end rigid portion 13 as a distal-end constituent, a first bending portion 14, a second bending portion 15, a flexible-tube distal end portion 16 as a halfway portion, a flexible-tube bending portion 17, and a flexible tube portion 18 continuously arranged in this order from the distal end side thereof.

According to the first embodiment, the first bending portion 14 includes a plurality of continuously-set bending pieces (not shown) which are bent in the up/down and left/right directions. The second bending portion 15 includes a plurality of continuously-set bending pieces (not shown) which are bent in the up/down direction (or left/right direction). The flexible-tube bending portion 17 includes a plurality of continuously-set bending pieces (not shown) which are bent in the left/right direction (or up/down direction).

The universal cord 12 is extended from the side portion of the operating portion 11. Light guide fibers are inserted in the universal cord 12 to transmit illuminating light. A light-source connector 19 is detachably connected to the light source device 4, and is arranged to a proximal end portion of the universal cord 12.

The light source device 4 comprises: a lamp 4a which generates the illuminating light and a condensing lens 4b. The illuminating light generated from the lamp 4a passes through the condensing lens 4b and is condensed to the end surface of a light guide cap 4c projected from the light-source connector 19.

The video processor 5 controls an image pick-up device incorporated in the observing unit 2, which will be described later, and performs the signal processing for generating a video signal based on an image signal which is photoelectrically converted by the image pick-up device.

The monitor 6 receives the video signal that is subjected to the signal processing by the video processor 5, and displays the observation image on the screen of the monitor 6. The observation image displayed on the monitor 6 is recorded by the VTR deck 7 and the video disc 8 and the like. The observation image displayed on the monitor 6 can be printed-out by the video printer 9.

Figure 2:
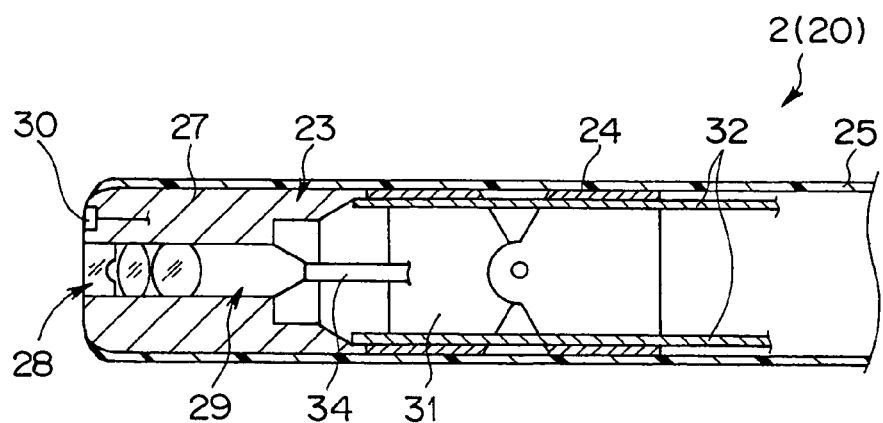
FIG. 2 is a diagram for explaining the structure of a distal end side of the an inserting portion of the observing unit.
Figure 3:
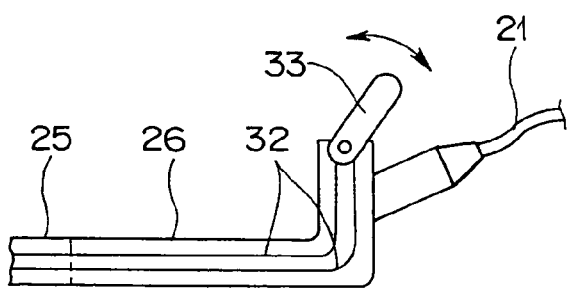
FIG. 3 is a diagram for explaining the structure of a proximal end side of the inserting portion of the observing unit.

Referring to FIGS. 2 and 3, the unit inserting portion 20 of the observing unit 2 comprises: an observing unit portion 23 and a unit joint piece 24 which form the distal end side thereof; a soft elongated sheath portion 25; and a proximal-end operating portion 26 forming the proximal end portion.

The proximal-end operating portion 26 is substantially L-shaped, for example. The distal end portion of the sheath portion 25 covers the unit joint piece 24 and the observing unit portion 23, and the proximal end portion of the sheath portion 25 covers the distal end portion of the proximal-end operating portion 26.

The observing unit portion 23 has a unit main body 27. The unit main body 27 comprises: objective lenses 28 forming the observing optical system; and an image pick-up device 29 having an image pick-up surface of an image pick-up element (not shown) at the image forming positions of the objective lenses 28. On the distal-end surface of the unit main body 27, a single or a plurality of LED illuminations 30 are arranged. Further, at the proximal end portion of the unit main body 27, a distal-end joint piece 31 is fixed. The distal end portion of the unit joint piece 24 is rotatably connected to the proximal end portion of the distal-end joint piece 31.

A distal end portion of an operating wire 32 is fixed to the distal end portion of the distal-end joint piece 31. The operating wire 32 is inserted in the unit joint piece 24 and the sheath portion 25, and a proximal end portion of the operating wire 32 is fixed to a unit main-body operating lever (hereinafter, abbreviated to an operating lever) 33. The operating lever 33 is rotatably arranged to the proximal-end operating portion 26 as shown by an arrow. The operating lever 33 is rotated and thus the operating wire 32 is drawn, thereby forming a bending mechanism portion in which the distal end portion of the observing unit 2 is changed to be straight or be bent.

A signal cable 34 is extended from the proximal end portion of the image pick-up device 29. A power cable is extended from the LED illuminations 30. The power cable and the signal cable 34 pass through the unit joint piece 24, the sheath portion 25, and the scope cable 21, and a proximal end portion of the signal cable 34 is electrically connected to the video connector 22.

An optical image at the portion illuminated by the LED illuminations 30 is formed onto the image pick-up surface of the image pick-up element arranged to the observing unit 2, is converted into an electric signal, and is transmitted to the video processor 5. The transmitted signal is converted into a video signal by the video processor 5 and is displayed on the screen of the monitor 6.

Figure 4:
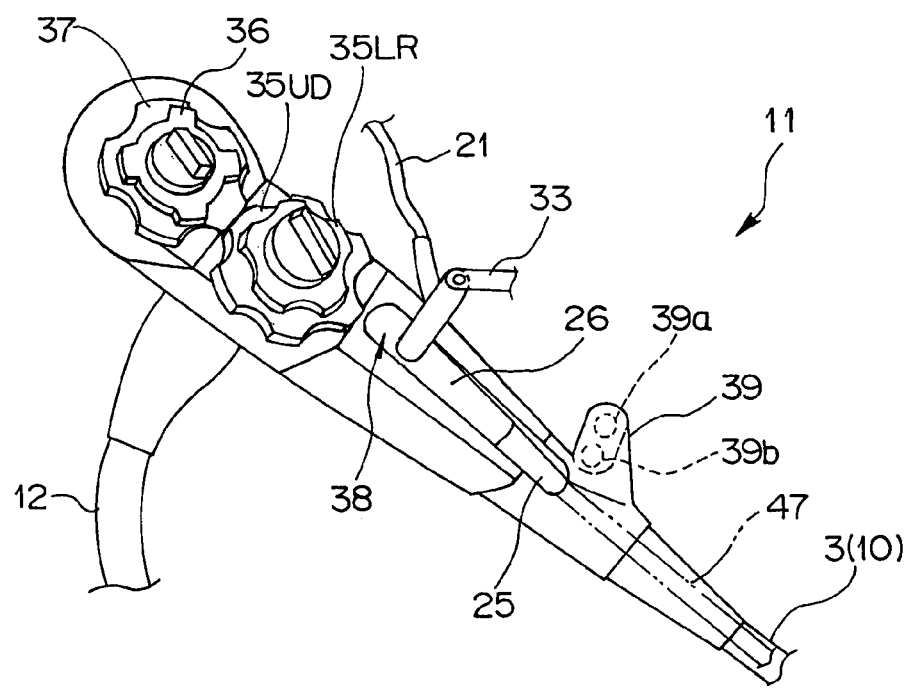
FIG. 4 is a diagram for explaining the structure of an operating portion of the unit inserting tool.

Referring to FIG. 4, the operating portion 11 comprises bending knobs 35UD and 35LR, and bending knobs 36 and 37. The bending knob 35UD is a knob which bends the first bending portion 14 in the up/down direction. The bending knob 35LR is a knob which bends the first bending portion 14 in the left/right direction. The bending knob 36 is a knob which bends the second bending portion 15 in the up/down direction. The bending knob 37 is a knob which bends the flexible-tube bending portion 17 in the left/right direction. The operator operates the bending knobs 35UD, 35LR, 36, and 37, thereby independently bending the first bending portion 14, second bending portion 15, and flexible-tube bending portion 17.

A treatment tool lead-in portion 39 is arranged on the side of the distal end of the operating portion 11. The treatment tool lead-in portion 39 comprises: a first treatment tool lead-in port 39a and a second treatment tool lead-in port 39b. The first treatment tool lead-in port 39a is communicated with a first treatment tool inserting channel (refer to reference numeral 50a in FIG. 5) arranged to the inserting portion 10, which will be described later. The second treatment tool lead-in port 39b is communicated with a second treatment tool inserting channel (refer to reference numeral 50b in FIG. 5) arranged to the inserting portion 10, which will be described later.

At the side surface portion of the operating portion 11, for example, a long hole for unit that is long and thin in the longitudinal direction (hereinafter abbreviated to a long hole) 38 is arranged. The long hole 38 is an optical unit guiding port which guides the observing unit 2 to a unit inserting channel 47, and the proximal-end operating portion 26 of the observing unit 2 can be arranged to the long hole 38.

Figure 5:
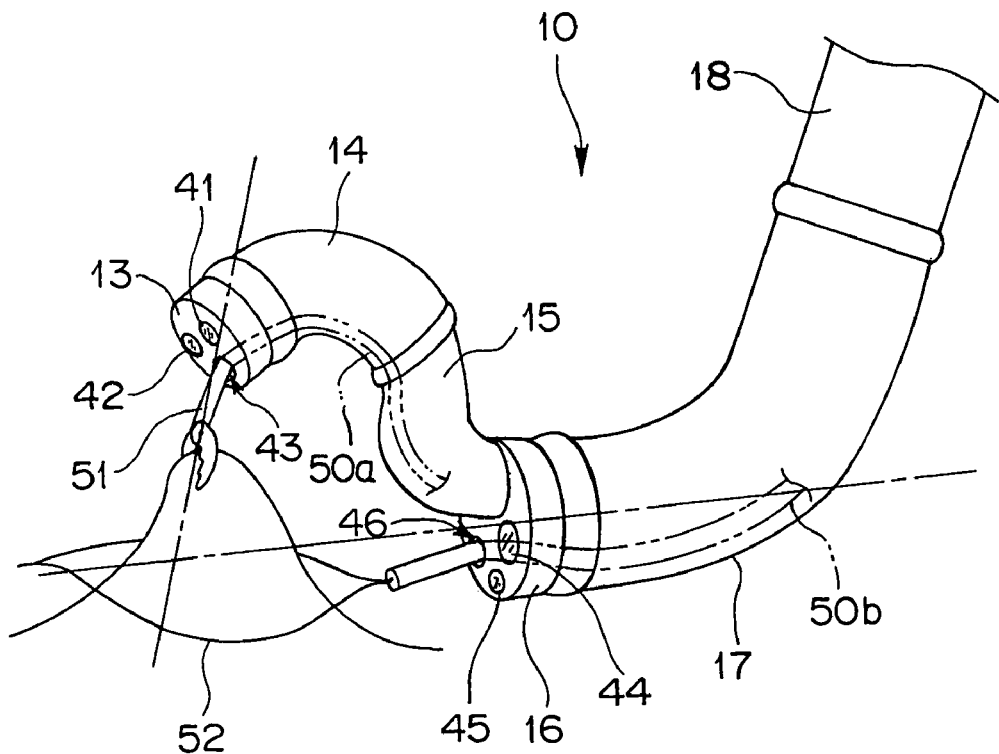
FIG. 5 is a perspective view for explaining the structure and the operation of the distal end side of the endoscope.

Referring to FIG. 5, the distal-end surface of the distal-end rigid portion 13 comprises: an observing lens cover (hereinafter, abbreviated to a distal-end observing cover) 41 as an observing window; an illuminating lens cover (hereinafter, abbreviated to a distal-end illuminating cover) 42 as an illuminating window; and a distal end opening 43 as a treatment tool lead-out port which is communicated with the first treatment tool inserting channel 50a from which grip forceps 51, or the like, as an endoscope treatment tool, inserted from the first treatment tool lead-in port 39a, are guided.

The proximal end portion of the second bending portion 15 is fixed onto the distal-end surface of the flexible-tube distal end portion 16. Further, the distal-end surface of the flexible-tube distal end portion 16 comprises: an observing lens cover (hereinafter, abbreviated to an observing cover at a halfway portion) 44 as an observing window; an illuminating lens cover (hereinafter, abbreviated to an illuminating cover at a halfway portion) 45 as an illuminating window; and a flexible-tube opening 46, as a treatment tool lead-out port, which is communicated with the second treatment tool inserting channel 50b from which a high-frequency snare 52, or the like, is guided, as a treatment tool for endoscope, which is inserted from the second treatment tool lead-in port 39b.

The bending knobs 35UD and 35LR are rotated, thereby bending the first bending portion 14 in the up/down direction and the left/right direction. The bending knob 36 is rotated, thereby bending the second bending portion 15 in the up/down direction. The bending knob 37 is rotated, thereby bending the flexible-tube bending portion 17 in the left/right direction.

In this embodiment, the unit inserting tool 3 is provided such that the optical axes of the observing cover 41 at the distal-end and the observing cover 44 at the halfway portion are parallel to the direction of the longitudinal axis of the unit inserting tool 3 in the linear state of the unit inserting tool 3.

Figure 6:
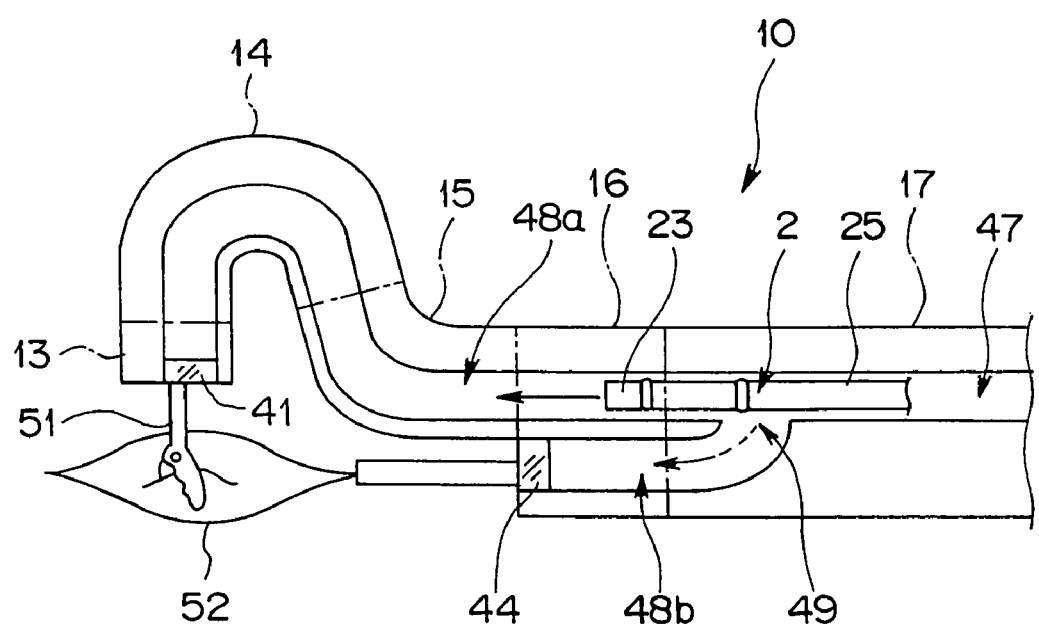
FIG. 6 is an explanatory diagram for explaining the structure and the operation of the distal end side of the endoscope, including a part of the cross section.

Referring to FIGS. 5 and 6, the first bending portion 14 is bent in the down direction, and the second bending portion 15 is bent in the up direction as the opposite direction of the bending direction of the first bending portion 14. Consequently, the treatment tool lead-out direction of the distal end opening 43 as shown by a chain line can be set to be vertical to the central axis as shown by a chain line of the flexible-tube-distal end portion 16.

Referring to FIG. 6, a unit inserting channel 47 communicated with the long hole 38 is arranged in the inserting portion 10. The observing unit 2 is inserted in the unit inserting channel 47. A branching portion 49 is formed at the halfway portion of the unit inserting channel 47. At the branching portion 49, the unit inserting channel 47 is branched into a first inserting channel 48a in the direction of the distal-end observing cover 41 and a second inserting channel 48b in the direction of the observing cover 44 at the halfway portion. According to the first embodiment, the branching portion 49 is arranged in the flexible-tube bending portion 17.

The observing unit 2 is inserted and arranged in the unit inserting channel 47 and, simultaneously, the proximal-end operating portion 26 is slid and moved along the long hole 38 in the long hole 38. Consequently, the observing unit 2 advances and returns. When the distal-end surface of the observing unit 2 is at the position of the branching portion 49, the operating lever 33 arranged to the proximal-end operating portion 26 is operated if necessary. Then, the distal end portion of the observing unit 2 changes to be straight or be bent, and the observing unit 2 is selectively guided to the side of the first inserting channel 48a shown by a solid arrow or the side of the second inserting channel 48b shown by a broken arrow.

With the image observed by the image pick-up device 29 which picks-up the image of the portion illuminated by the LED illuminations 30, it is checked to see if the distal-end surface of the distal-end rigid portion of the observing unit 2 is at the position of the branching portion 49. That is, the operator selectively performs the bending operation of the operating lever 33 while observing the observation image transmitted to the monitor 6 from the observing unit 2. Thus, the operator can freely insert the observing unit 2 into the desired first inserting channel 48a or second inserting channel 48b.

The observing unit 2 is inserted in the first inserting channel 48a side, and the distal-end surface of the observing unit 2 is closely arranged to the end surface of the distal-end observing cover 41, thereby performing the observation via the distal-end observing cover 41. The observing unit 2 is inserted to the second inserting channel 48b side, and the distal-end surface of the observing unit 2 is arranged to the end surface of the observing cover 44 at the halfway portion, thereby performing the observation via the observing cover 44 at the halfway portion.

That is, the monitor 6 displays, on the screen, the observation image of the examined portion captured by the observing unit 2 via the distal-end observing cover 41 and the observing cover 44 at the halfway portion.

The distal-end surface of the light guide fibers forming the illuminating optical system is arranged to the distal-end illuminating cover 42 and the illuminating cover 45 at the halfway portion arranged to the distal-end rigid portion 13 and the flexible-tube distal end portion 16. Therefore, the illuminating light condensed to the end surface of the light guide cap 4c is transmitted via the light guide fibers which are inserted in the universal cord 12, the operating portion 11, and the inserting portion 10, and is irradiated to the examined portion via the distal-end illuminating cover 42 and the illuminating cover 45 at the halfway portion.

A description is given of the operation of the endoscope apparatus having the endoscope 1 with the above structure.

First, the observing unit 2 is inserted in the unit inserting channel 47 from the long hole 38 formed to the operating portion 11 of the unit inserting tool 3. In this case, the video processor 5 is operated and the LED illuminations 30 is lit-on. Further, the image pick-up device 29 enters the image pick-up state. Then, the monitor 6 displays, on the screen, the observation image captured by the image pick-up device 29 of the observing unit 2 which moves in the unit inserting channel 47. The observing unit 2 is arranged in the first inserting channel 48a while observing the observation image displayed on the monitor 6, and the preparation for the observation is set via the distal-end observing cover 41 arranged to the distal-end rigid portion 13.

Next, the light source device 4 is operated, thereby irradiating the illuminating light from the distal-end illuminating cover 42 and the illuminating cover 45 at the halfway portion. The inserting portion 10 of the unit inserting tool 3 is inserted in the body cavity while observing the observation image picked-up via the distal-end observing cover 41, which is displayed on the screen of the monitor 6. In this case, the bending knobs 35UD, 35LR, 36, and 37 arranged to the operating portion 11 are properly operated.

Referring to FIGS. 5 and 6, the distal-end surface of the inserting portion 10 faces the target portion. For the purpose of incising the tissue, the grip forceps 51 are inserted from the first treatment tool lead-in port 39a of the treatment tool lead-in portion 39, and the high-frequency snare 52 is inserted from the second treatment tool lead-in port 39b.

Then, the grip forceps 51 is guided into the body cavity from the distal end opening 43 of the distal-end rigid portion 13. The high-frequency snare 52 is guided from the flexible-tube opening 46 of the flexible-tube distal end portion 16.

The high-frequency snare 52 is position-adjusted while observing the observation image which is picked-up via the distal-end observing cover 41, displayed on the monitor 6. Then, the observing unit 2 arranged in the second inserting channel 48b is moved in the second inserting channel 48b by operating the proximal-end operating portion 26 and the operating lever 33, thereby displaying the observation image, which is picked-up via the observing cover 44 at the halfway portion, on the screen of the monitor 6.

Then, the treatment portion is gripped by operating the grip forceps 51 while observing the observation image. After that, the pick-up operation is performed by the moving operation or the bending operation of the grip forceps 51, and the incision using the high-frequency snare 52 starts. Upon incision, the observing unit 2 is moved to the first inserting channel 48a side or the second inserting channel 48b side if necessary.

Upon incision, the observing unit 2 is moved to the first inserting channel 48a, thereby observing the entire incision portion from the top. It is checked to see if the incision portion and the range are proper, or to which degree the incision advances based on the stop degree of the high-frequency snare 52. As a result, more reliable incision is possible.

According to the first embodiment, when the observing direction is changed by moving the observing unit 2 to the first inserting channel 48a or the second inserting channel 48b, the treatment tool is not operated or the position and posture of the unit inserting tool 3 is not adjusted. That is, the inserting state of the inserting portion 10 of the unit inserting tool 3 changes and the gripping state of the body tissue keeps constant. Then, the observing unit 2 is moved, thereby changing the observing direction. Therefore, the operability during the treatment is improved.

As mentioned above, the endoscope comprises: the observing unit with flexibility having the objective lenses and the image pick-up device; and the unit inserting tool having the inserting channels having the observing unit inserted therein at the inserting portion thereof. The branching portion is arranged to the inserting channels of the unit inserting tool. The observing covers having the closely arranged distal-end surface of the observing unit are arranged to the distal end portions of the branched inserting channels. Therefore, the observing unit inserted in the inserting channels is moved without changing the inserting state of the inserting portion of the unit inserting tool which is inserted in the body cavity and is bent. Thus, the observation images in the plurality of directions are obtained for the treatment.

The first bending portion arranged between the distal-end rigid portion and the flexible-tube distal end portion is bent down. The second bending portion is bent in the up direction. The plurality of bending portions are properly bent, thereby obtaining the desired observing state. Thus, the treatment tool guided from the distal end opening vertically advances and returns in the field of view through the observing window of the flexible-tube distal end portion. Further, the treatment tool guided from the flexible-tube opening vertically advances and returns in the field of view through the observing window at the distal end portion.

In addition, the arrangement of the flexible-tube bending portion enables the free direction at the target portion of the flexible-tube opening arranged to the flexible-tube distal end portion as well as the distal end portion of the distal-end rigid portion. Thus, the operability in the treatment is further improved.

The increase in the number of bending portions enables the free setting in various directions of the treatment tool guided from the distal end opening or flexible-tube opening in the field of view for observation of the observing cover at the flexible-tube distal end portion. Thus, the operability in the treatment is improved.

In the first embodiment, the distal end opening 43 is provided in the distal-end rigid portion 13 and the flexible-tube opening 46 is provided in the flexible-line end portion 16, and the first treatment tool lead-in port 39a and the second treatment tool lead-in port 39b which correspond to the openings 43 and 36 respectively are provided in the treatment tool lead-in portion 39 of the operating portion 11. However, for example, for the use when a needle is pricked in an anatomically swollen and risen portion, so as to confirm whether the needle has completely passed through it to the back side thereof with the needle being pricked in the tissue, it is needed to have only an observing optical system which can come up around to the back side. In other words, the opening as the treatment tool lead-out portion for leading out the pricking needle provided in the unit inserting tool 3 may be provided either in the distal-end rigid portion 13 or in the flexible-tube distal end portion 16.

Also in the first embodiment, the first bending portion 14 and the second bending portion 15 are provided between the distal-end rigid portion 13 of the unit inserting tool 3 and the flexible-tube distal end portion 16, and the flexible-tube bending portion 17 is provided at the rear side of the flexible-tube distal end portion 16. However, it is possible to constitute the unit inserting tool by any other suitable combination of the bending portions, for example, by providing one of the first bending portion 14 and the second bending portion 15 between the distal-end rigid portion 13 and the flexible-tube distal end portion 16 or by providing one of the first bending portion 14 and the second bending portion 15 or three or more bending portions between the distal-end rigid portion 13 and the flexible-tube distal end portion 16 or by providing the flexible-tube bending portion 17 only at the rear side of the flexible-tube distal end portion 16.

According to the first embodiment, upon guiding the observing unit 2 arranged to the branching portion 49 of the unit inserting channel 47 to the first inserting channel 48a side or the second inserting channel 48b side, the operation of the operating lever 33 changes the distal end portion of the observing unit 2 to the bending state or straight state. Therefore, the unit joint piece 24, the distal-end joint piece 31, and the operating wire 32 are arranged to the distal-end side portion of the unit inserting portion 20 in the observing unit 2. Further, the operating lever 33 is arranged to the proximal end portion of the unit inserting portion 20. Thus, the structure of the observing unit 2 is complicated. The observing unit 2 is desired with the unit inserting portion 20 having the simple structure and the thin outer-diameter. The branching portion of the observing unit or inserting channel is structured as follows, thereby simplifying the structure of the observing unit 2 and making the outer diameter of the observing unit 2 thinner.

First, a description is given of the observing unit having the simple structure of the inserting portion therein with reference to FIGS. 7 to 10.

Figure 7:
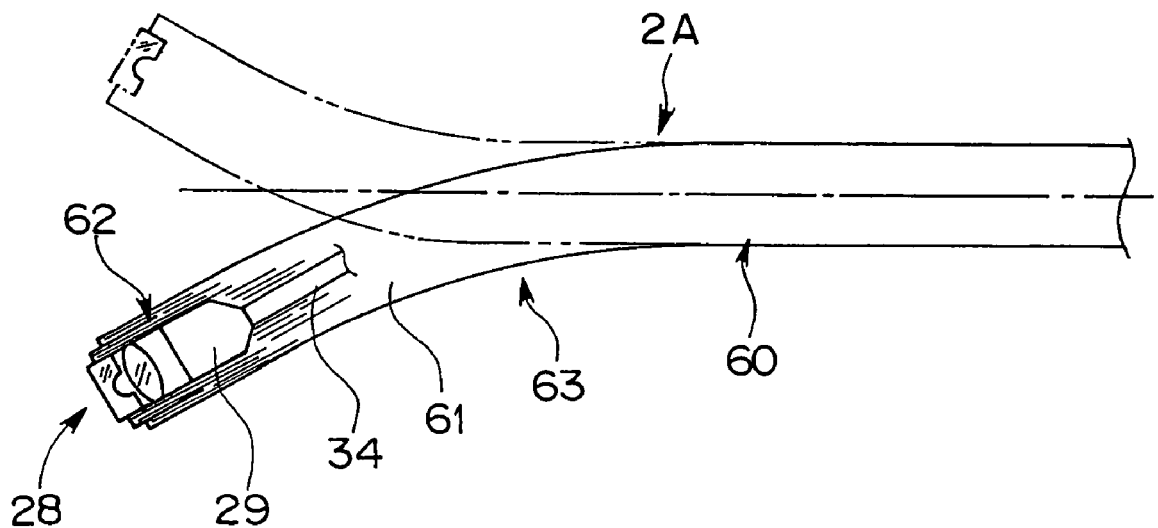
FIG. 7 is a diagram for explaining the observing unit having a bending proclivity portion.
Figure 8:
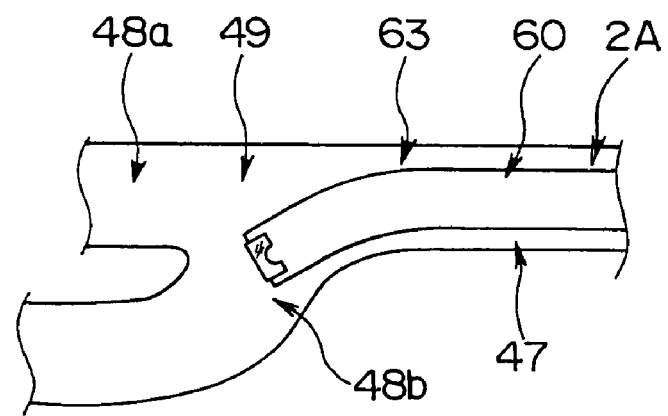
FIG. 8 is a diagram for explaining a state in which the observing unit is guided to a second inserting channel.
Figure 9:
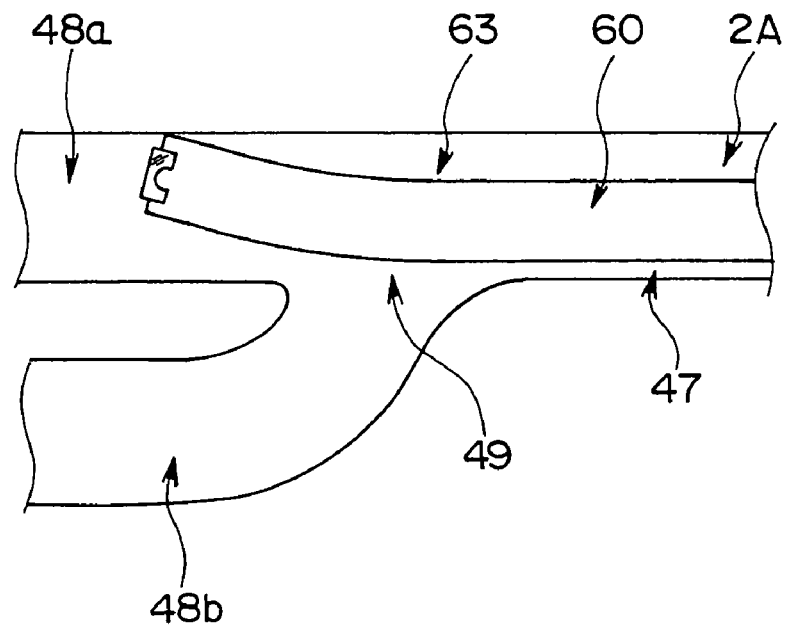
FIG. 9 is a diagram for explaining a state in which the observing unit is guided to a first inserting channel.

Referring to FIG. 7, an inserting portion 60 of an observing unit 2A comprises an elongated sheath portion 61. The sheath portion 61 comprises therein the objective lenses 28, the image pick-up device 29, and the signal cable 34, and further comprises light guide fibers 62 in place of the LED illuminations 30. The light guide fibers 62 are arranged around the objective lenses 28. A bending proclivity portion 63 is naturally bent in a single direction, and is previously arranged to the distal end portion of the inserting portion 60.

Thus, when the distal-end surface of the inserting portion 60 in the observing unit 2A is at the position of the branching portion 49 in the unit inserting channel 47, the twisting operation is performed by gripping the hand side (not shown), thereby changing the direction of the distal end portion of the observing unit 2A as shown by a chain double-dashed line.

Specifically, the twisting operation is performed when the distal-end surface of the observing unit 2A is at the position of the branching portion 49 in the unit inserting channel 47, thereby changing the observing unit 2A. That is, then, referring to FIG. 8, the distal-end surface of the observing unit 2A faces the second inserting channel 48b side. Alternatively, referring to FIG. 9, the distal-end surface of the observing unit 2A faces the side wall surface of the first inserting channel 48a. In this case, the monitor 6 displays, on the screen thereof, the observation image of the opening in the direction of the second inserting channel 48b, on which the distal-end surface of the observing unit 2A faces the second inserting channel 48b. Or, the monitor 6 displays, on the screen thereof, the observation image on which the side wall surface of the first inserting channel 48a is captured.

The operator grasps the position of the distal end of the observing unit 2A based on the observation image displayed on the monitor 6, and determines the inserting channel to be inserted. In the state in which the observation image of the opening is displayed on the screen of the monitor 6, the inserting portion 60 is pressed, thereby inserting the observing unit 2A into the second inserting channel 48b. In the state in which the observation image of the side wall surface is displayed on the screen of the monitor 6, the inserting portion 60 is pressed, thereby inserting the observing unit 2A in the first inserting channel 48a.

Figure 10:
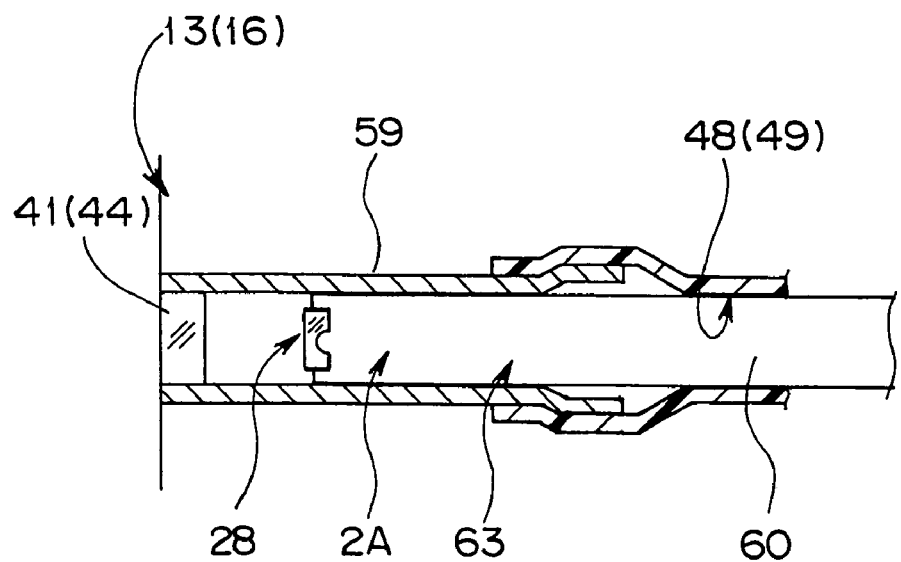
FIG. 10 is a diagram for explaining the operation of a guide pipe which is arranged near a lens cover.

Referring to FIG. 10, a guide pipe 59 is arranged at the predetermined position on the side of the proximal end surfaces of the distal-end observing cover 41 and the observing cover 44 at the halfway portion of the distal-end rigid portion 13 and the flexible-tube distal end portion 16. The distal end portion of the observing unit 2A is fit into the guide pipe 59, and the guide pipe 59 contains a rigid member. The distal end portion of the observing unit 2A is inserted in the guide pipe 59, thereby correcting the bending proclivity portion 63 of the sheath portion 61. Further, the distal-end surface of the observing unit 2A is closely arranged to the distal-end observing cover 41 and the observing cover 44 at the halfway portion. That is, the guide pipe 59 is arranged, thereby certainly ensuring the front field-of-view of the observing unit 2A to which the bending proclivity portion 63 is arranged.

The outer surface of the proximal end portion of the sheath portion 61 may have an index (not shown) for notifying the direction of the bending proclivity portion 63 of the sheath portion 61 so that the operator who grips the inserting portion 60 easily determines the position of the bending proclivity portion 63 arranged to the observing unit 2A.

Thus, when the observing unit 2A is inserted in the unit inserting channel 47 of the unit inserting tool 3, the inserting operation is performed by checking the index while grasping the direction of the bending proclivity portion 63 of the sheath portion 61. The operability for inserting the observing unit is improved.

By arranging the bending proclivity portion to the sheath portion in the observing unit, the inserting portion of the observing unit is simplified. The observing unit reaching the branching portion of the inserting channel is selectively guided to the first inserting channel side or the second inserting channel side by the twisting operation.

Figure 11:
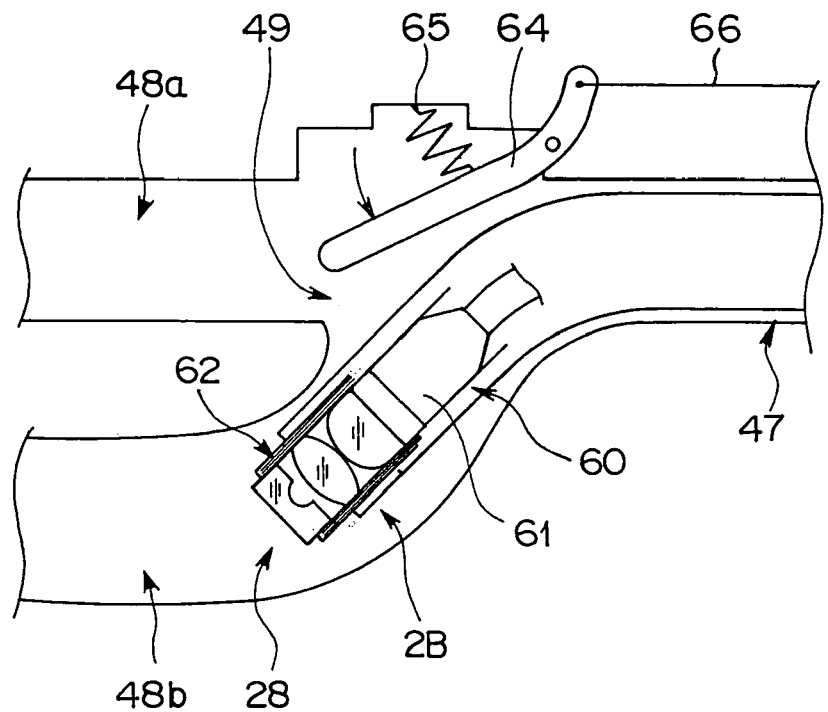
FIG. 11 is a diagram for explaining the structure of an inserting-channel switching mechanism and a state in which the observing unit is guided in the second inserting channel.
Figure 12:
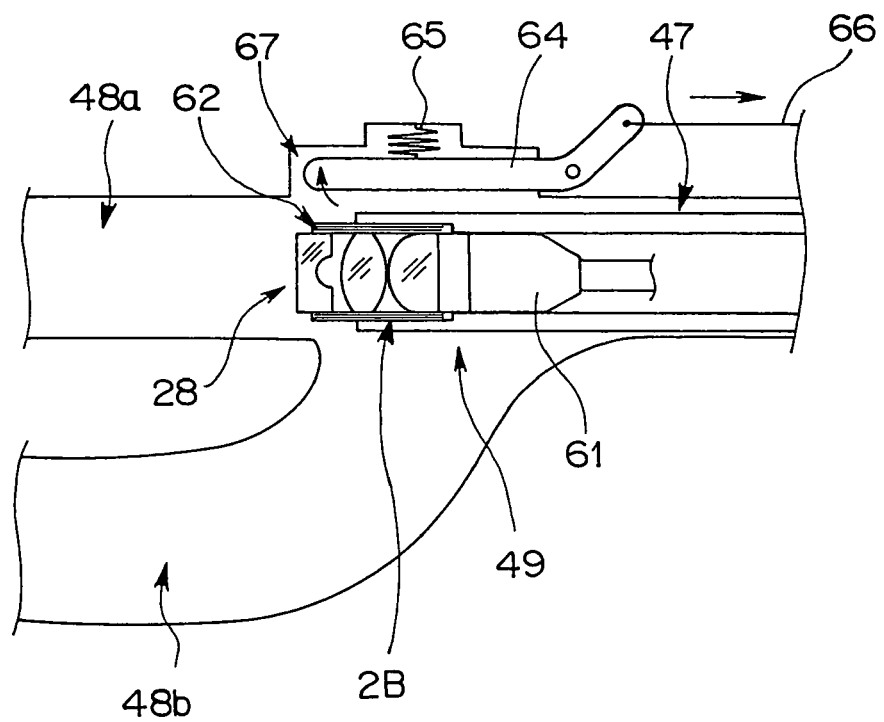
FIG. 12 is a diagram for explaining the structure of the inserting-channel switching mechanism and a state in which the observing unit is guided in the first inserting channel.

Next, a description is given of an inserting-channel switching mechanism arranged to the branching portion of the inserting channel of the unit inserting tool so as to simplify the structure of the inserting portion of the observing unit with reference to FIGS. 11 and 12.

Referring to FIG. 11, the inserting-channel switching mechanism is arranged to the branching portion 49. The inserting-channel switching mechanism mainly comprises: a rotating plate 64; a biasing member 65; and a drawing operating wire 66. The rotating plate 64 is rotatably arranged. The biasing member 65 is, for example, a spring member which biases the rotating plate 64 in a direction shown by an arrow. The drawing operating wire 66 is drawn, thereby moving the rotating plate 64 in the opposite arrow side against the biasing force of the biasing member 65.

When the drawing operating wire 66 in the inserting-channel switching mechanism is in the state in the diagram, the drawing operating wire 66 is not drawn. Therefore, the rotating plate 64 is arranged at the closing position for covering the opening into the first inserting channel 48*a* by the biasing force of the biasing member 65. Therefore, when the observing unit 2B at the position of the branching portion 49 in the unit inserting channel 47 is pressed and advanced, the rotating plate 64 prevents the insertion in the first inserting channel 48*a* and the observing unit 2B is guided in the second inserting channel 48*b*.

On the contrary, when the drawing operating wire 66 is drawn, referring to FIG. 12, the rotating plate 64 is moved against the biasing force of the biasing member 65, and the rotating plate 64 is accommodated in a concaved portion 67 arranged to the branching portion 49. Then, an opening into the first inserting channel 48*a* appears. Thus, when the observing unit 2B at the position of the branching portion 49 in the unit inserting channel 47 is pressed and advanced, the observing unit 2B is straightly moved in the unit inserting channel 47 and is guided to the side of the first inserting channel 48*a* side. That is, according to the first embodiment, the observing unit 2B is structured without providing the unit joint piece 24, the distal-end joint piece 31, the operating wire 32, the operating lever 33, and the bending proclivity portion 63.

As mentioned above, the branching portion of the inserting channel comprises the inserting-channel switching mechanism comprising the rotating plate, the biasing member, and the drawing operating wire. The operation of the drawing operating wire on the hand side switches the opening in the first inserting channel to the opening state or closing state, thereby selectively guiding the observing unit at the position of the branching portion of the inserting channel into the first inserting channel or the second inserting channel.

The structure of the inserting portion in the observing unit is further simplified.

Figure 13:
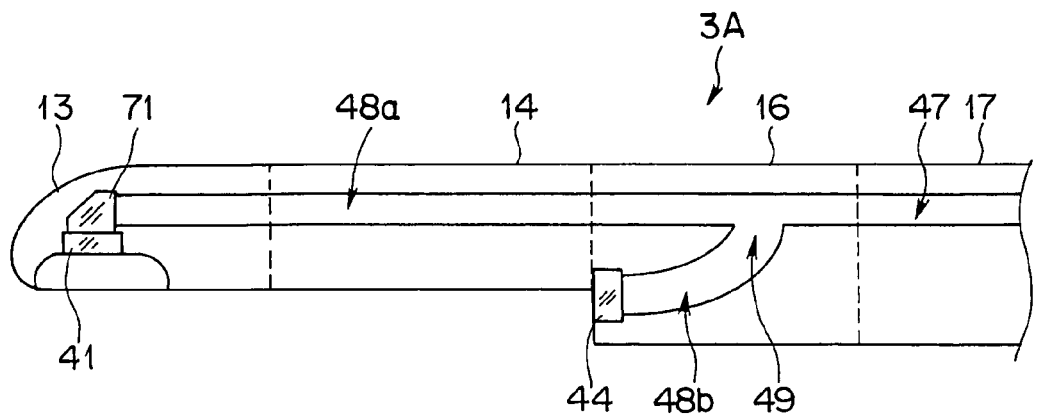
FIG. 13 is a diagram for explaining the schematic structure of the unit inserting tool.
Figure 14:
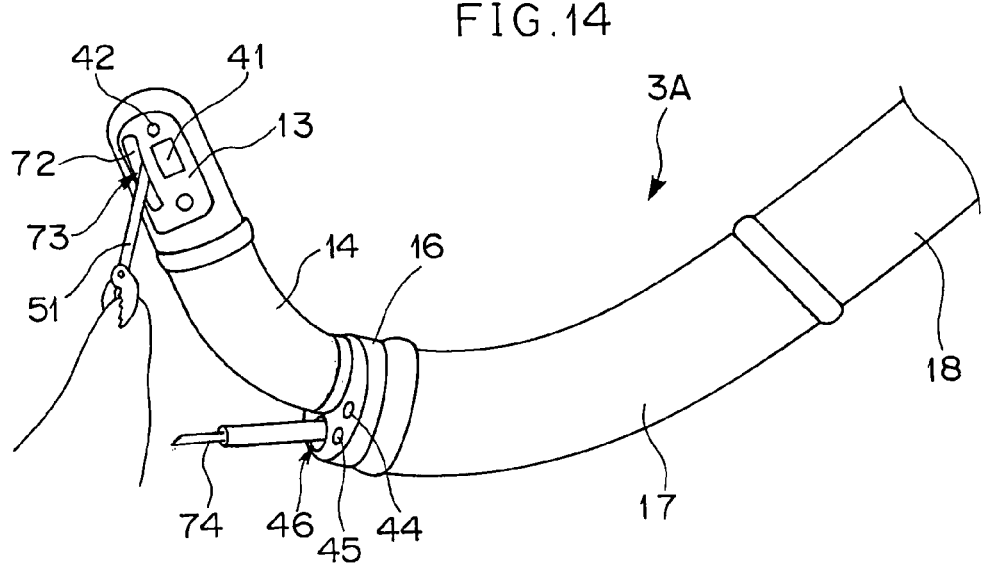
FIG. 14 is a diagram for explaining one example of the operation of the unit inserting tool.
Figure 15:
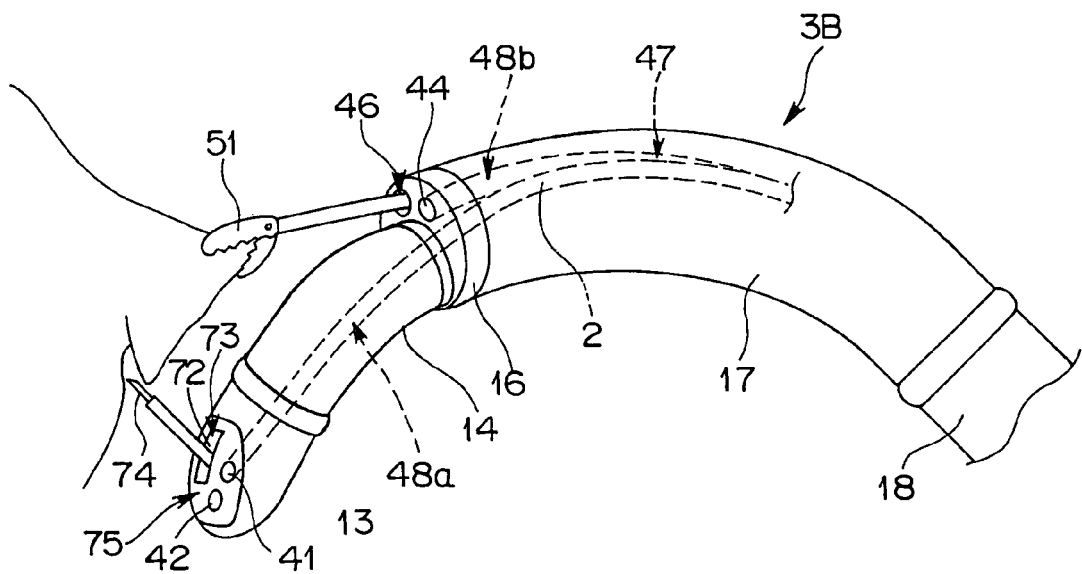
FIG. 15 is a diagram for explaining another example of the operation of the unit inserting tool.

A description is given of another structure of the unit inserting tool with reference to FIGS. 13 to 15.

Referring to FIG. 13, in a unit inserting tool 3A according to the first embodiment, the distal-end observing cover 41 is arranged to the side surface of the distal-end rigid portion 13, in place of the arrangement of the distal-end observing cover 41 onto the distal-end surface of the distal-end rigid portion 13. A prism 71 for bending the optical axis of the observation image incident from the distal-end observing cover 41 by an angle of 90° is arranged to the distal end portion of the first inserting channel 48*a*.

In other words, in this embodiment, the distal-end observing cover 41 is provided such that the optical axis thereof is perpendicular to the direction of the longitudinal axis of the unit inserting tool 3 in the linear state of the unit inserting tool 3, and the observing cover at the halfway portion 44 is provided such that the optical axis thereof is parallel to the direction of the longitudinal axis of the unit inserting tool 3 in the linear state of the unit inserting tool 3.

Thus, the distal-end surface of the observing unit inserted in the first inserting channel 48*a* is closely arranged to the prism 71, thereby performing the observation in the side view direction. The observing unit is inserted in the second inserting channel 48*b*, thereby closely arranging the distal-end surface of the observing unit to the observing cover 44 at the halfway portion. Similarly, the observation is performed in the direct view direction.

With the structure, referring to FIG. 14, the side surface of the distal-end rigid portion 13 has the distal-end observing cover 41 and a distal end opening 73 having the arrangement of a stand-up base 72 for projecting the treatment tool substantially in the same direction as the field-of-view direction of the side view. Further, one of the first bending portion 14 and the second bending portion 15 is arranged between the distal-end rigid portion 13 and the flexible-tube distal end portion 16. Then, as shown in FIG. 5, the first bending portion 14 is bent in the down direction. Only the first bending portion 14 is bent without bending the second bending portion 15 in the opposite direction of the bending direction of the first bending portion 14, thereby easily setting the treatment tool lead-out direction of the distal end opening 73 and the axial direction of the flexible-tube distal end portion 16 to be substantially vertical to each other.

With the structure, the grip forceps 51 are projected in the side-view observing direction from the distal end opening 73 of the distal-end rigid portion 13, thereby setting the gripping state of the body tissue. The grip forceps 51 are set to be close or the second bending portion 15 is bent in the up direction, thereby picking-up the body tissue in the direction vertical to the axial direction of the flexible-tube distal end portion 16. Upon picking-up the body tissue, the observing unit is arranged to the first inserting channel 48*a* side, thereby observing the picking-up state of the body tissue while the grip forceps 51 grip the body tissue.

In the picking-up state, an electric knife 74 is led out from the flexible-tube opening 46 of the flexible-tube distal end portion 16, thereby incising the picked-up body tissue. In the incision, the observing unit is moved to the observing cover 44 at the halfway portion on the side of the second inserting channel 48*b* side. Thus, the body tissue is directly observed from the distal-end surface of the flexible-tube distal end portion 16, and the incision with the electric knife 74 is observed.

After that, the observing unit is moved and arranged again to the distal-end observing cover 41 on the side of the first inserting channel 48*a*, and the body tissue is incised while observing the body tissue from the gripping side of the incised tissue. Thus, the incising range and the state around the incising portion are certainly checked. The observing direction is changed and the more reliable incision is executed by moving the observing unit while keeping the gripping state of the body tissue constant without adjusting the position and posture of the unit inserting tool 3A.

Referring to FIG. 15, the distal-end observing cover 41 arranged to a unit inserting tool 3B is arranged to an inclined surface 75 of the distal-end rigid portion 13, and a prism (not shown) may be arranged to the distal end portion of the first inserting channel 48a to bend the optical axis of the observation image incident from the distal-end observing cover 41.

Thus, it is possible to observe the perspective view of the body tissue by closely arranging, to the prism (not shown), the distal-end surface of the observing unit inserted in the first inserting channel 48a. Further, it is possible to observe the direct view of the body tissue by inserting the observing unit in the second inserting channel 48b and then by closely arranging the observing unit to the observing cover 44 at the halfway portion. With the structure, one of the first bending portion 14 and the second bending portion 15 is arranged between the distal-end rigid portion 13 and the flexible-tube distal end portion 16.

Referring to FIG. 15, the grip forceps 51 are projected forward from the flexible-tube opening 46 of the flexible-tube distal end portion 16 and thus the body tissue is picked up. In this state, the electric knife 74 is led-out from the distal end opening 73 of the distal-end rigid portion 13, and the picked-up body tissue is incised. In this case, the observing unit is properly moved and arranged to the distal-end observing cover 41 on the side of the second inserting channel 48b and to the observing cover 44 at the halfway portion on the side of the first inserting channel 48a. Thus, the same operations and advantages as those shown in FIG. 14 are obtained.

According to the first embodiment, the image pick-up device of the observing unit picks-up the image and the observation image of the examined portion illuminated with the illuminating light from the illuminating optical system arranged to the unit inserting tool is observed. However, the observing unit is not the illuminating optical system which illuminates the narrow range with the small amount of light for checking the branching portion. The observing unit comprises an endoscope unit having the illuminating optical system and the observing optical system for observation with the lens structure for widely illuminating the body cavity. The endoscope unit may be inserted in the inserting channel.

With the above-mentioned structure, the distal-end surface of the endoscope unit is closely arranged to the lens cover of the first inserting channel or the second inserting channel. Thus, the illuminating light from the illuminating optical system in the endoscope unit is illuminated to the examined portion, and the observing optical system in the endoscope unit obtains the observation image.

The endoscope unit is inserted in the unit inserting channel. The light guide fibers and the illuminating cover forming the illuminating optical system are unnecessary from the unit inserting tool. The inserting channel corresponding to the endoscope unit is possible with the thick diameter.

The second embodiment of the present invention will be described with reference to FIGS. 16 to 20.

Figure 16:
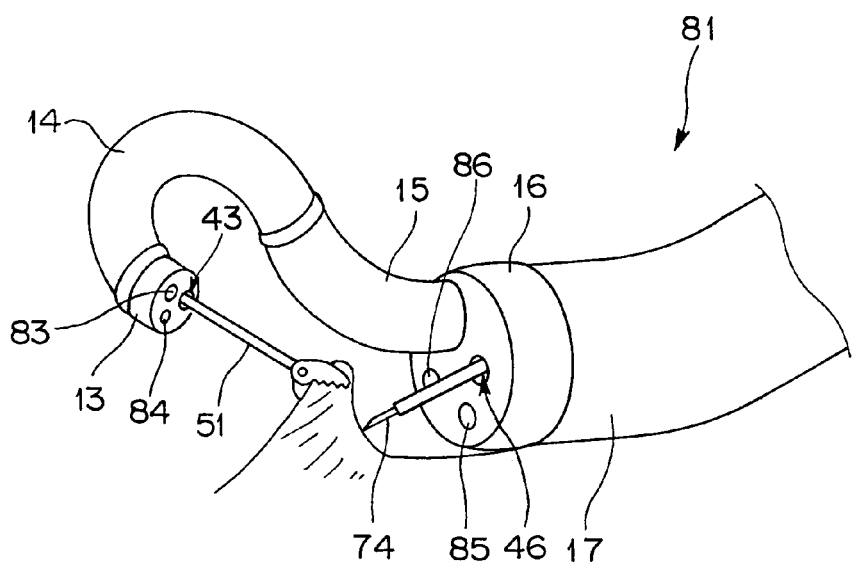
FIG. 16 is a diagram for explaining the structure and the operation of an endoscope having an observing optical system, an illuminating optical system, and a treatment tool lead-out port which are arranged to a distal-end surface of a distal rigid portion and a distal-end surface of a flexible-tube distal end portion.
Figure 17:
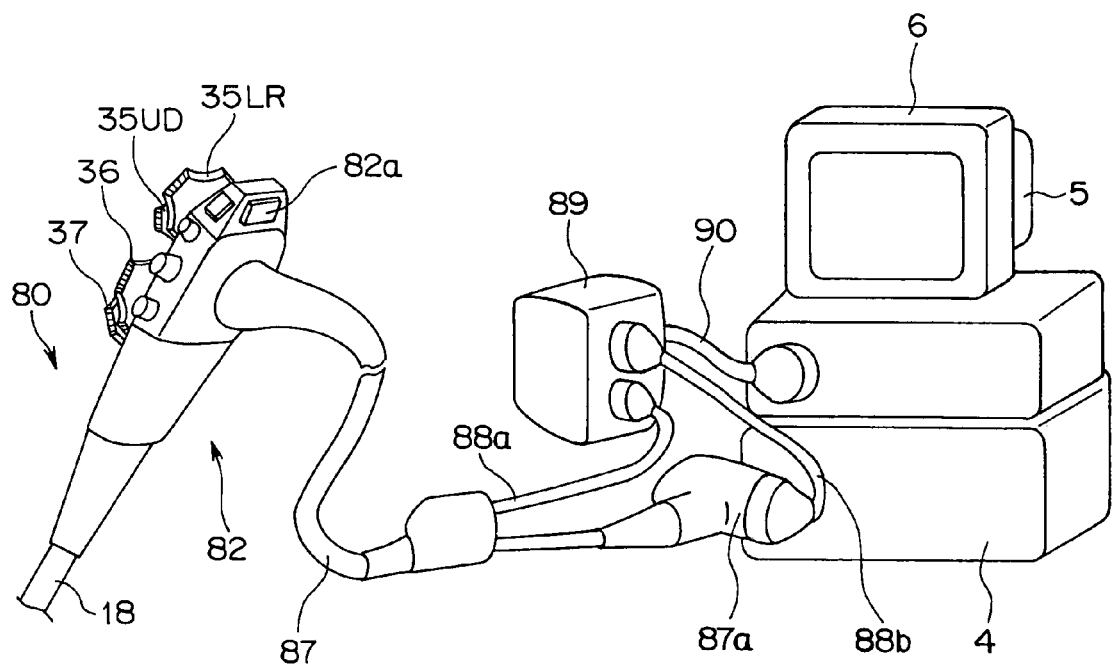
FIG. 17 is a diagram for explaining one example of the structure of a video processor and a monitor corresponding to the endoscope shown in FIG. 16.

Referring to FIGS. 16 and 17, similarly to the unit inserting tool 3, an inserting portion 81 of an endoscope 80 according to the second embodiment comprises, in the order of the distal end side: the distal-end rigid portion 13; the first bending portion 14; the second bending portion 15; the flexible-tube distal end portion 16; the flexible-tube bending portion 17; and the flexible tube portion 18. The bending knobs 35UD, 35LR, 36, and 37 are arranged to an operating portion 82 which functions as a grip portion at the position of a proximal end of the inserting portion 81. The first bending portion 14, the second bending portion 15, and the flexible-tube bending portion 17 are independently bent by the operation of the bending knobs 35UD, 35LR, 36, and 37.

A distal-end observing-system cover 83, a distal-end illuminating-system cover 84, and the distal end opening 43 are arranged onto a distal-end surface of the distal-end rigid portion 13. An observing-system cover 85 at the halfway portion, an illuminating-system cover 86 at the halfway portion, and the flexible-tube opening 46 are arranged to the distal-end surface of the flexible-tube distal end portion 16. Objective lenses and an image pick-up device (which are not shown) forming the observing optical system are arranged on the side of the proximal ends of the distal-end observing-system cover 83 of the distal-end rigid portion 13 and the observing-system cover 85 at the halfway portion of the flexible-tube distal end portion 16.

The optical image passes through the distal-end observing-system cover 83 and the observing-system cover 85 at the halfway portion, and is formed to the image pick-up device. Then, the optical image is photoelectrically converted into an electric signal by the image pick-up device and is transmitted to the video processor 5 via signal cables (not shown) extended from the image pick-up device.

Specifically, the signal cables extended from the image pick-up device are inserted in the inserting portion 81, the operating portion 82, and a universal cord 87 extended from the side portion of the operating portion 82. One signal cable is transmitted to a switching device 89 via a first electric cable 88a. The other signal cable is inputted to the switching device 89 via a second electric cable 88b that is detachably connected to the side portion of an endoscope connector 87a detachably connected to the light source device 4. The switching device 89 selectively transmits the electric signal transmitted via the respective signal cables and the electric cables 88a and 88b to the video processor 5 by operating a switching means arranged to the operating portion 82, for example, an image change-over switch 82a. The switching device 89 is connected to the video processor 5 via an image cable 90.

A description is given of the operation of an endoscope apparatus having an endoscope 80 with the above-mentioned structure.

In the endoscope 80, the observing-system cover 85 at the halfway portion and the like of the flexible-tube distal end portion 16 faces any examined portion in the large organ such as the stomach by bending the flexible-tube bending portion 17 forming the inserting portion 81. The inserting portion 81 independently bends the first bending portion 14 and the second bending portion 15 and thus the distal-end surface of the distal-end rigid portion 13 is easily vertical to the direction of the inserting axis of the flexible-tube distal end portion 16.

Referring to FIG. 16, the grip forceps 51 are projected from the distal end opening 43 of the distal-end rigid portion 13 and the tissue is picked-up. The electric knife 74 is projected from the flexible-tube opening 46 of the flexible-tube distal end portion 16, and the down portion gripped by the grip forceps 51 is incised. Then, the image change-over switch 82a is properly operated, and the following advantages are expected.

The monitor 6 displays, on the screen, the observation image via the distal-end observing-system cover 83 arranged to the distal-end rigid portion 13, thereby checking the state of the gripped portion or incising range.

Meanwhile, the observation image via the observing-system cover 85 at the halfway portion of the flexible-tube distal end portion 16 is displayed by switching and then the treatment is performed while observing the incising state with the electric knife 74.

The image pick-up device is arranged to the distal-end rigid portion and the flexible-tube distal end portion, and a change-over switch is arranged to the operating portion so as to switch the observation image displayed on the monitor. Thus, the observation image displayed on the monitor is promptly switched to the observation image which is captured by the image pick-up device at the flexible-tube distal end portion or to the observation image captured by the image pick-up device at the distal-end rigid portion. A reliable treatment is promptly performed.

The distal-end surfaces of light guide fibers face the distal-end illuminating-system cover 84 and the illuminating-system cover 86 at the halfway portion, and the light guide fibers are inserted in the universal cord 87. The endoscope connector is connected to the light source device 4, thereby supplying the illuminating light via the light guide fibers.

Figure 18:
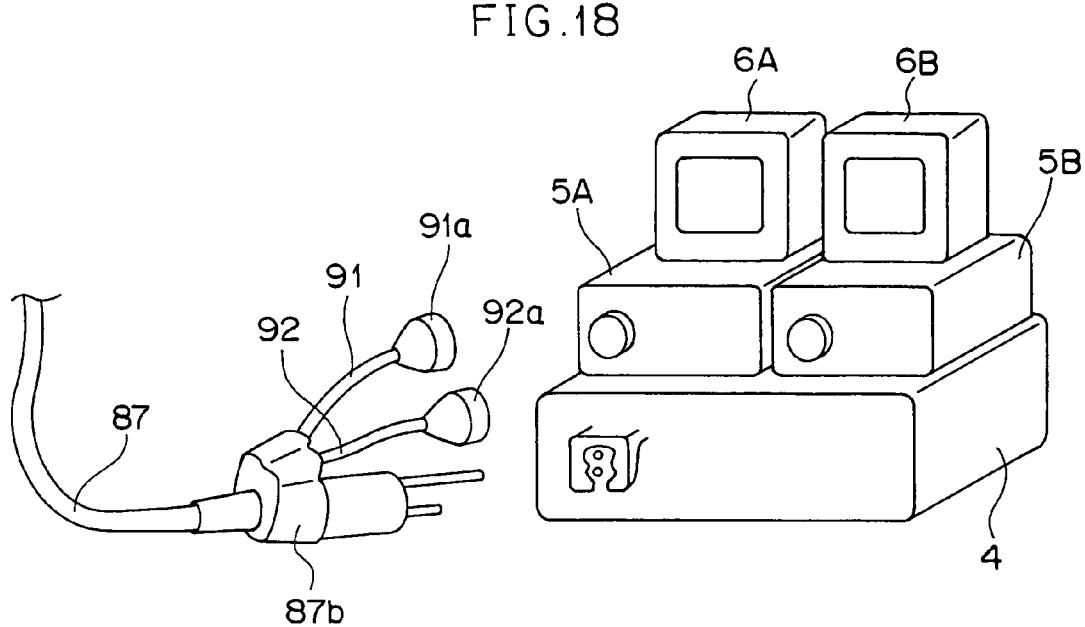
FIG. 18 is a diagram for explaining another example of the structure of the video processor and the monitor corresponding to the endoscope shown in FIG. 16.

Referring to FIG. 18, the signal cables, which are inserted in the universal cord 87 and are extended to the endoscope connector 87b, may be extended as two electric cables 91 and 92 from the side portion of the endoscope connector 87b. In this case, electric cables 91 and 92 are connected to video processors 5A and 5B which are independent via connectors 91a and 92a. The observation images picked-up by the image pick-up device via the distal-end observing-system cover 83 or the observing-system cover 85 at the halfway portion are displayed independently and simultaneously on the screens of monitors 6A and 6B corresponding to the video processors 5A and 5B. Thus, both the observation images are observed and the treatment is performed without switching operation.

Further, the field-of-view direction of the distal-end observing-system cover 83 at the position of the distal-end rigid portion 13 may be the side view direction. In this case, the first bending portion 14 is arranged between the distal-end rigid portion 13 and the flexible-tube distal end portion 16, similarly to the unit inserting tool 3A shown in FIG. 14. Thus, the same operation and advantages according to the first embodiment are obtained.

Figure 19:
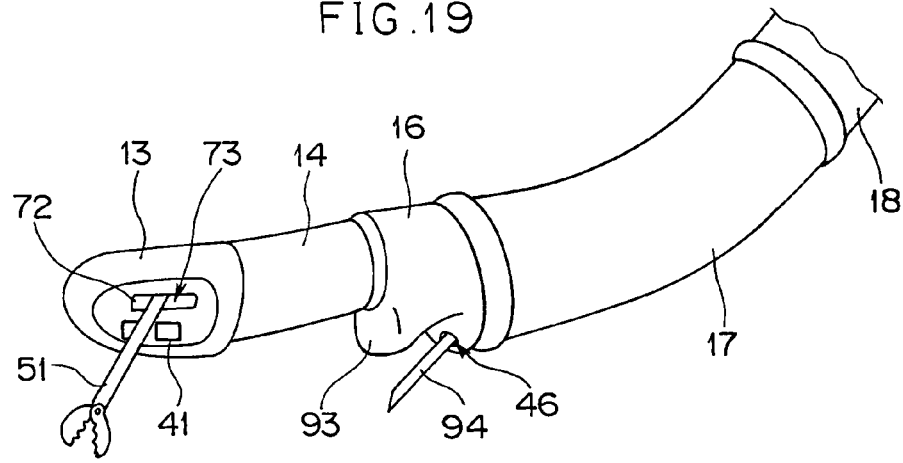
FIG. 19 is a diagram for explaining an endoscope having an ultrasonic observing portion on the distal end side of the flexible-tube distal end portion.
Figure 20:
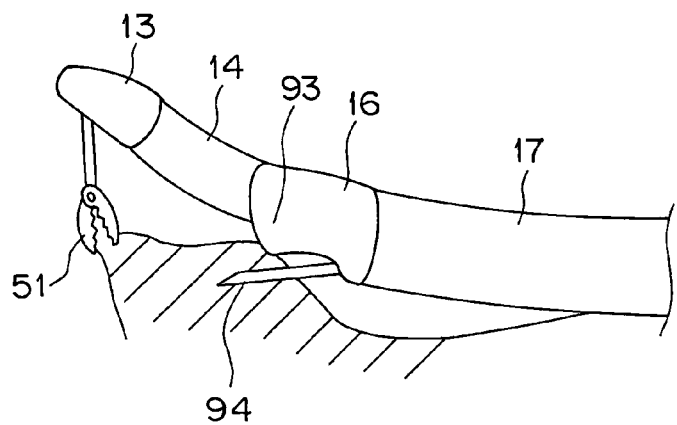
FIG. 20 is a diagram for explaining the operation of the endoscope shown in FIG. 19.

Referring to FIGS. 19 and 20, an ultrasonic observing portion 93 for sector scanning with the ultrasonic waves is arranged to the flexible-tube distal end portion 16, in place of the observing-system cover 85 at the halfway portion and the illuminating-system cover 86 at the halfway portion. Echo data obtained by the ultrasonic observing portion 93 is transmitted to an ultrasonic observing device (not shown), and an ultrasonic tomographic image may be displayed on a screen of a monitor (not shown).

With the structure, the grip forceps 51 guided from the distal-end rigid portion 13 pick-up the body tissue, a pricking needle 94 is projected from the flexible-tube opening 46 of the flexible-tube bending portion 17, and the pricking needle 94 is pricked in the body tissue. Then, with the ultrasonic tomographic image obtained by the ultrasonic observing portion 93, it is checked to see where the needle tip pricked to the body tissue reaches in the depth.

The third embodiment of the present invention will be described with reference to FIGS. 21 to 23.

Figure 21:
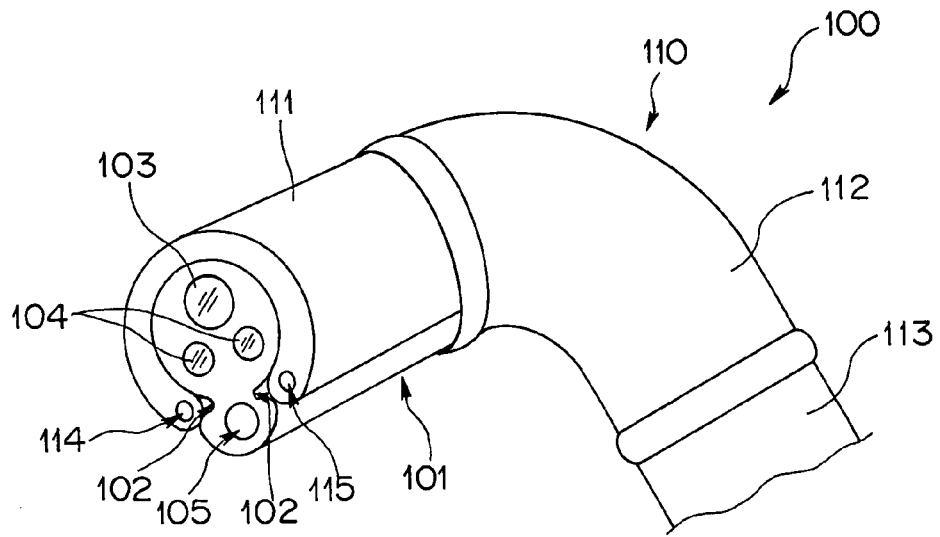
FIG. 21 is a perspective view for explaining the structure of an inserting-portion distal end portion of an endoscope for treatment.
Figure 22:
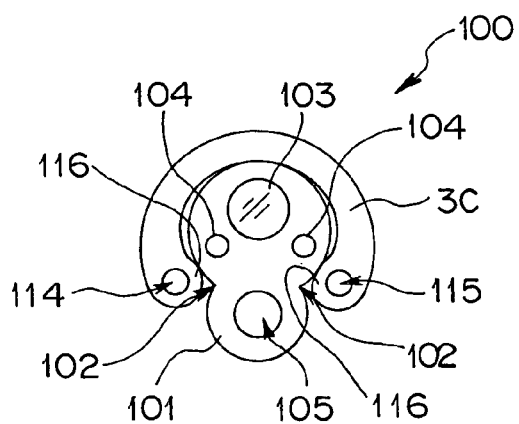
FIG. 22 is a front view for explaining the structure of the inserting-portion distal end portion of the endoscope for treatment.
Figure 23:
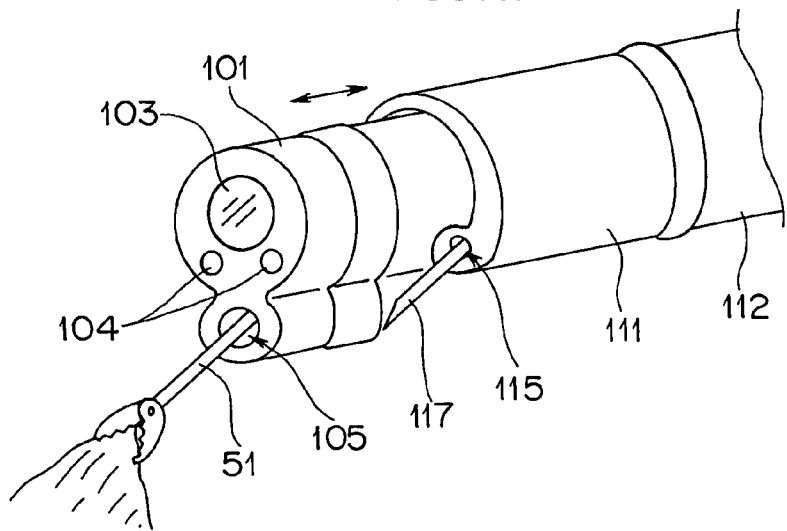
FIG. 23 is a diagram for explaining the operation of the endoscope for treatment.

Referring to FIGS. 21 and 22, an endoscope 100 according to the third embodiment comprises: an elongated endoscope unit 101 with the flexibility; and a unit inserting tool 110 to which the endoscope unit 101 is arranged.

The unit inserting tool 110 has the cross-sectional shape of the inserting portion that is substantially C-shaped. The unit inserting tool 110 comprises, in order of the distal end side thereof: a distal-end rigid portion 111; a bending portion 112; and a flexible tube portion 113. For example, the pair of treatment tool guiding ports 114 and 115 are arranged to the distal-end surface of the distal-end rigid portion 111. The bending portion 112 is bent in the left/right direction. Reference numeral 116 denotes an engaging projected portion which is projected to the inner peripheral surface.

The endoscope unit 101 has the cross-sectional shape that is substantially 8-shaped. The endoscope unit 101 has a bending portion (not shown) which is bent in the up/down direction. The unit inserting tool 110 has a concaved portion 102 to which the engaging projected portion 116 is arranged. The distal-end surface of the endoscope unit 101 has an observing system cover 103 forming the observing optical system, an illuminating system lens cover 104 forming the illuminating optical system, and a treatment tool lead-out port 105.

The endoscope unit 101 advances and returns independently of the unit inserting tool 110. That is, referring to FIG. 21, the distal-end surface of the endoscope unit 101 matches, on the surface, the distal-end surface of the unit inserting tool 110. From this state, referring to FIG. 23, the distal-end surface of the endoscope unit 101 is projected from the distal-end surface of the unit inserting tool 110. When the endoscope unit 101 is projected, the bending operation is performed.

The operation of the endoscope 100 with the above structure will be described.

First, the endoscope 100 is inserted to the target portion while the distal-end surface of the endoscope unit 101 matches, on the surface, the distal-end surface of the unit inserting tool 110. The observation image picked-up via the observing system cover 103 is checked on the screen of the monitor and the endoscope unit 101 is projected from the distal-end surface of the unit inserting tool 110.

Next, the grip forceps 51 are led-out from the treatment tool lead-out port 105. The observation image displayed on the monitor is observed and the body tissue is gripped. Then, the endoscope unit 101 is returned and the body tissue is picked-up.

Next, a knife 117 for incision is led-out from one of the treatment tool lead-out ports 114 and 115 arranged to the unit inserting tool 110. The knife 117 for incision is led-out in front of the distal-end surface of the endoscope unit 101, thereby displaying, on the screen of the monitor, the body tissue which is raised and the knife 117 for incision. In this state, the hand side operation is properly performed and the body tissue is incised.

As mentioned above, the endoscope unit advances and returns independently of the unit inserting tool. Further, the treatment tool lead-out ports are arranged having the lead-out directions matching the endoscope unit and the unit inserting tool. Thus, it is possible to always observe the treatment tool led-out from the treatment tool lead-out port of the unit inserting tool and the endoscope unit from the constant direction with the image of field-of-view of the endoscope unit, and the two treatment tools are easily cooperated.

The fourth embodiment of the present invention will be described with reference to FIGS. 24 to 33.

Figure 24:
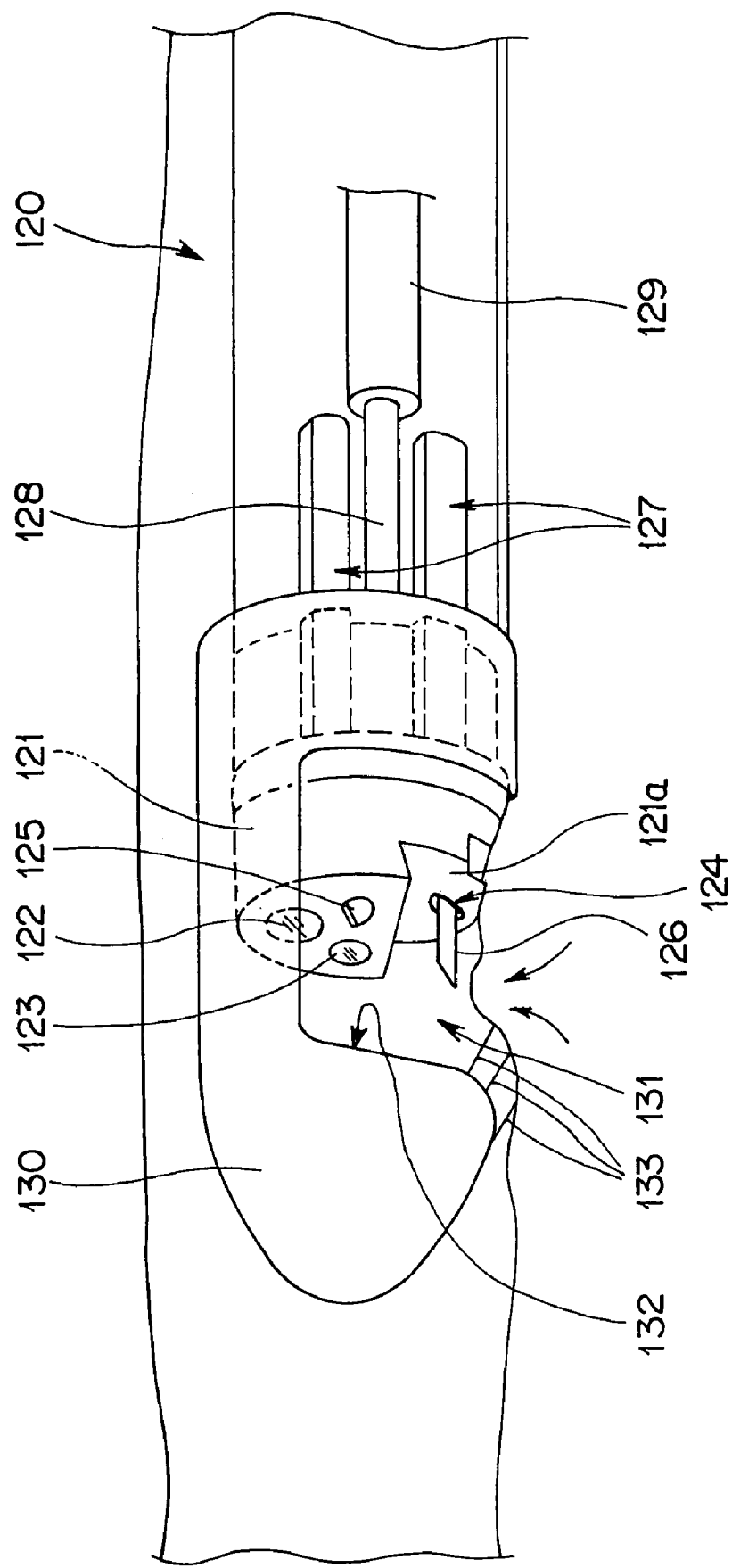
FIG. 24 is a diagram for explaining a distal-end hood which is arranged to a distal-end rigid portion forming an endoscope so as to freely advance and return.

Referring to FIG. 24, a distal-end rigid portion 121 of an endoscope 120 comprises: an observing cover 122, an illuminating cover 123, a hole 124 for inserting the pricking needle; and a cleaning nozzle 125 for cleaning the observing cover 122. A pricking needle 126 is inserted and arranged in the hole 124 for inserting the pricking needle.

Objective lenses and the image pick-up device (which are not shown) are arranged on the proximal side of the observing cover 122, and signal cables are extended from the image pick-up device. Therefore, the optical image formed to the image pick-up device via the observing cover 122 is photo-electrically converted into an image signal. The image signal is transmitted to the video processor via the signal cables, and is subjected to the signal processing, thereby obtaining a video signal.

Figure 25:
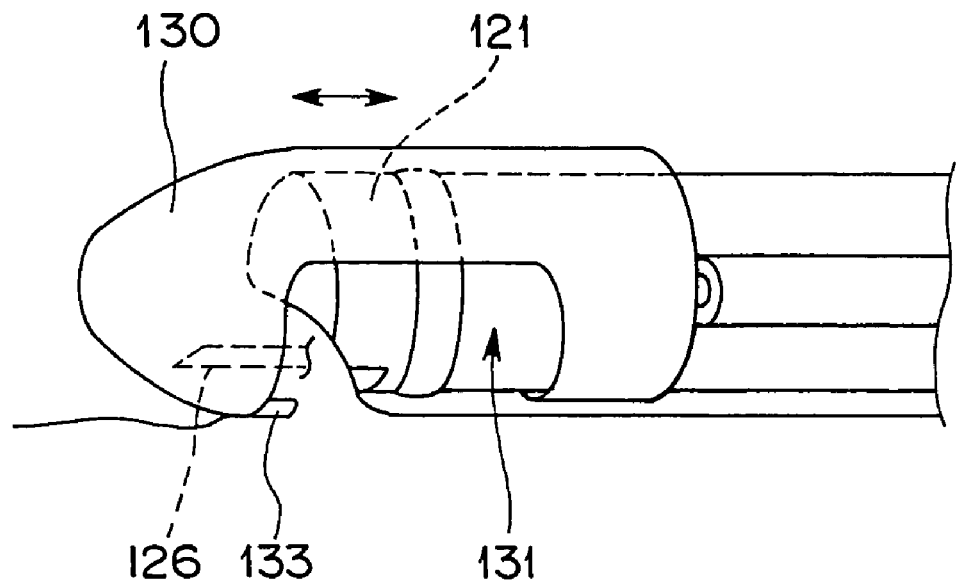
FIG. 25 is a diagram for explaining a state in which the body wall is drawn into a hood concaved portion of a distal-end hood.

Referring to FIGS. 24 and 25, a distal-end hood 130 is covered and is arranged to the distal-end rigid portion 121. The distal-end hood 130 advances and returns along a plurality of elongated hood guides 127 in the inserting axial direction formed to the side surface portion of the distal-end rigid portion 121. A distal end portion of a hood drawing wire (hereinafter, abbreviated to a drawing wire) 128 is fixed to the proximal end portion of the distal end hood 130. The proximal end portion of the hood drawing wire 128 is inserted in a wire guide tube 129 arranged to the side peripheral surface of the inserting portion of the endoscope 120 and is fixed to a drawing knob 161 arranged to an operating portion shown in FIG. 31, which will be described later. Therefore, the operator operates the drawing knob 161, thereby advancing and returning the hood drawing wire 128. The distal-end hood 130 advances and returns as shown by an arrow in FIG. 25.

A hood concaved portion 131 is arranged to the side peripheral portion of the distal-end hood 130, and comprises a side opening perpendicular to the longitudinal axial direction of the endoscope 120. A distal-end surface 121a of the distal-end rigid portion 121 is arranged in the hood concaved portion 131.

A plurality of claw-shaped hooks 133 are projected to the hand side direction and is arranged to an inner wall surface 132 on the distal end side of the hood concaved portion 131. When the distal-end hood 130 is moved to the hand side, the claw-shaped hooks 133 pull the body tissue in the hood concaved portion 131. Therefore, the hook distal end portion is sharply formed so as to hook the body tissue to the claw-shaped hooks 133, and the distal end of the claw-shaped hooks 133 is formed with the bending proclivity so as to be directed to the notch bottom surface side in the hood concaved portion 131.

Figure 26:
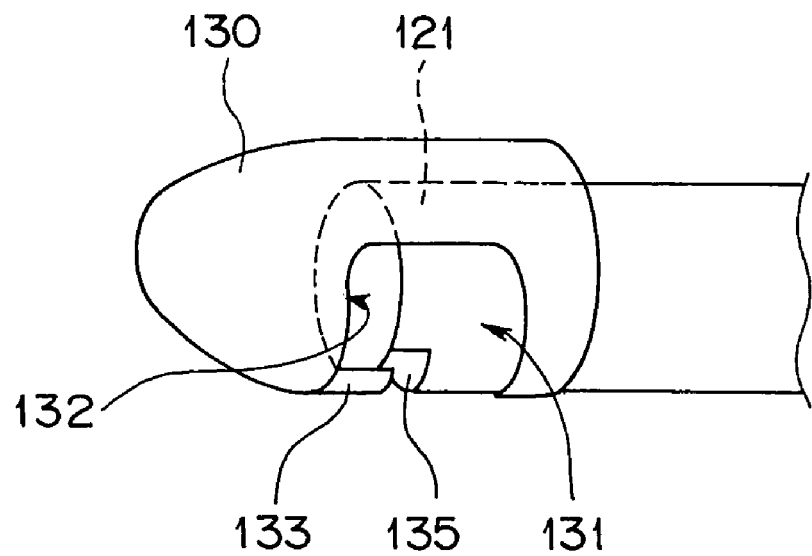
FIG. 26 is a diagram for explaining a state in which the distal-end hood is moved to the most proximal-end side.

Referring to FIG. 26, when the distal-end hood 130 is drawn and arranged at the most proximal-end side, the inner wall surface 132 on the distal end side is set to be positioned near the distal-end surface without being close to the distal-end surface of the distal-end rigid portion 121. An elongated hook accommodating groove 135 is formed in the axial direction corresponding to the claw-shaped hooks 133 on the distal-end surface of the distal-end rigid portion 121. Therefore, when the distal-end hood 130 is positioned at the most proximal-end side, the claw-shaped hooks 133 are accommodated in the hook accommodating groove 135.

Figure 27A:
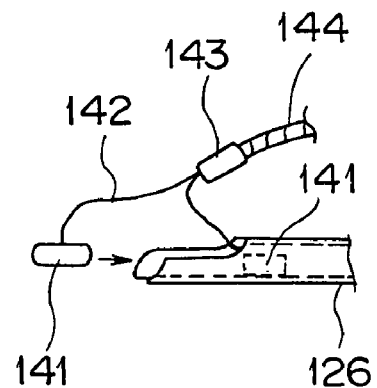
FIG. 27A is a diagram for explaining a pipe-shaped pricking needle and T-bars which are arranged in through-holes of the pricking needle.
Figure 27B:
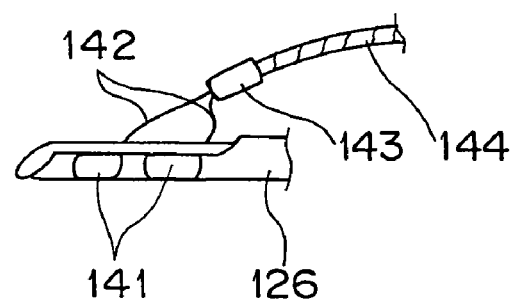
FIG. 27B is a diagram for explaining the relationship among a connecting thread for connecting the T-bars, a tightening member, and a tightening tool.
Figure 27C:
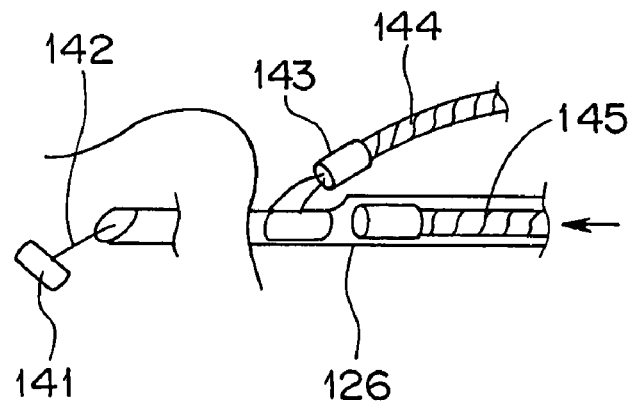
FIG. 27C is a diagram for explaining a pusher which is arranged in the through-hole of the pricking needle.

Referring to FIGS. 27A to 27C, the pricking needle 126 comprises a hollow pipe. Two T-bars 141 are inserted in the through-hole of the pricking needle 126. The T-bars 141 are connected by a connecting thread 142. A tightening member 143 is arranged to a halfway portion of the connecting thread 142. The tightening member 143 is engaged with the distal end of a tightening tool 144, and the tightening tool 144 is operated from the operating portion side. Thus, the distance between the T-bars 141 can be narrowed.

Referring to FIG. 27C, a pusher 145 extended to the operating portion is included on the rear side of the T-bars 141 arranged in the through-hole of the pricking needle 126. The pusher 145 is pressed out by the operator, thereby pressing, to the outside, the T-bars 141 arranged in the through-hole of the pricking needle 126.

Figure 28:
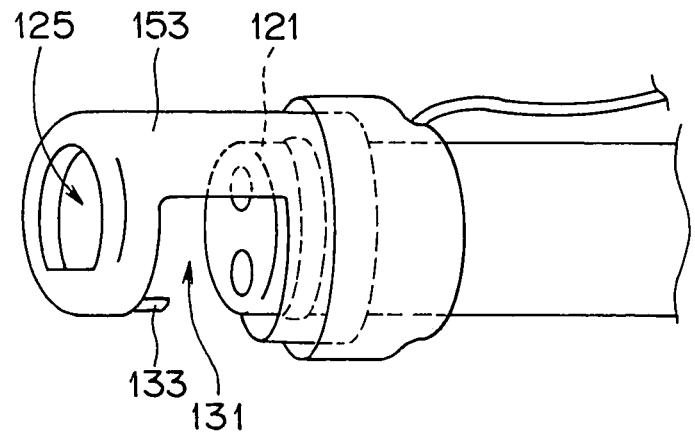
FIG. 28 is a diagram for explaining another structure of the distal-end hood.

According to the forth embodiment, the distal-end hood 130 contains a transparent member for ensuring the field of view. Referring to FIG. 28, a distal-end hood 153 with the opening having forward a hood opening portion 152 is formed for ensuring the field of view.

The advancing and returning operation of the distal-end hood 130 is not limited to the advancing and returning operation of the hood drawing wire 128. For example, the advancing and returning operation of the distal-end hood 130 may advance and return with the air pressure as shown in FIGS. 29 and 30.

Figure 29:
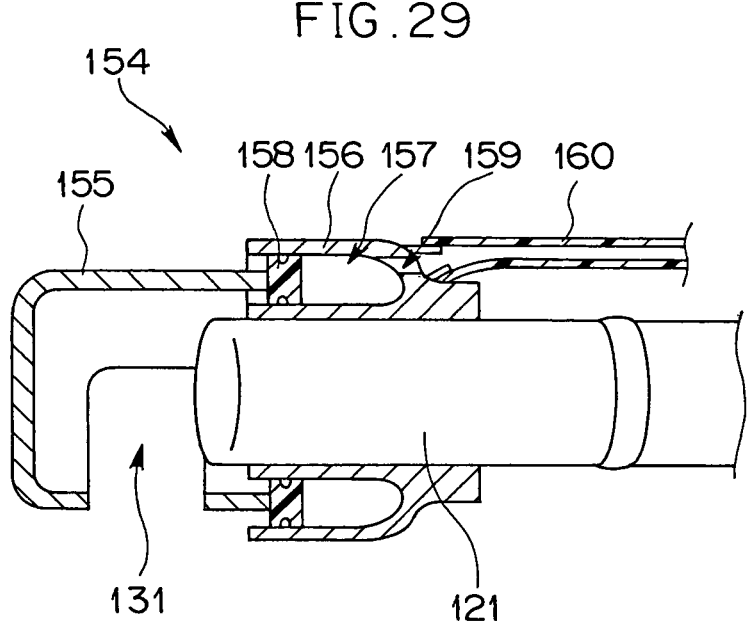
FIG. 29 is a diagram for explaining another mechanism in which the distal-end hood advances and returns.
Figure 30:
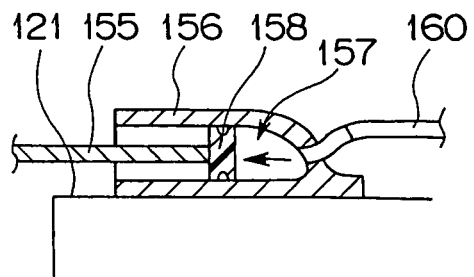
FIG. 30 is a diagram for explaining a state in which a cylinder head is moved in accordance with the increase in inner pressure.

Referring to FIG. 29, according to the fourth embodiment, a distal-end hood 154 comprises a hood portion 155 and a hood base 156 to which the hood portion 155 is slidably arranged. A cylinder portion 157 is arranged to the hood base 156. A cylinder head 158 containing rubber is arranged to the end portion of the hood portion 155.

The cylinder head 158 is slidably arranged to the cylinder portion 157. The space surrounded by the cylinder portion 157 and the cylinder head 158 is closed from the outside. A port 159 communicated with the closed space is arranged to the hood base 156. One end portion of an air feed tube 160 is connected to the port 159. The other end portion of the air feed tube 160 is connected to a pump or a manually operated syringe (not shown) as inner pressure operating means.

The air is fed to the cylinder portion 157 by the pump, thereby increasing the pressure in the closed space. Then, when the hood portion 155 is moved to the hand side, referring to FIG. 30, the cylinder head 158 is moved forward as shown by an arrow in accordance with the increased pressure in the closed space. Thus, the hood portion 155 integrated to the cylinder head 158 is moved forward and the hood concaved portion 131 is opened. When the pressure in the closed space decreases, the cylinder head 158 is moved to the proximal end. Thus, the hood portion 155 is moved to the hand side and the hood concaved portion 131 is closed again.

Figure 31:
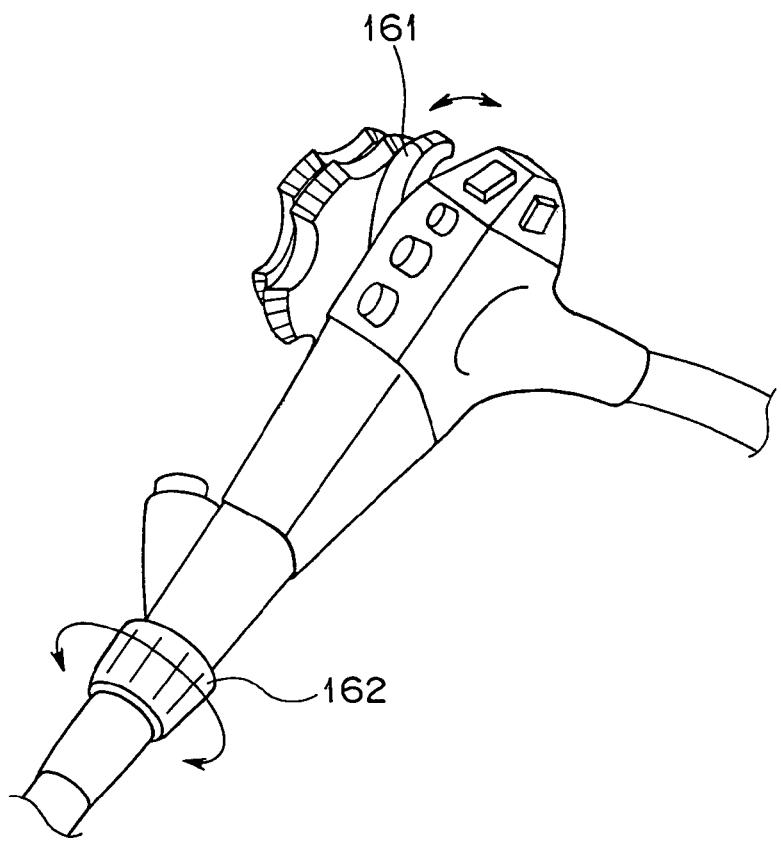
FIG. 31 is a diagram for explaining the operation of a drawing knob and a rotating ring which are arranged to an operating portion.
Figure 32:
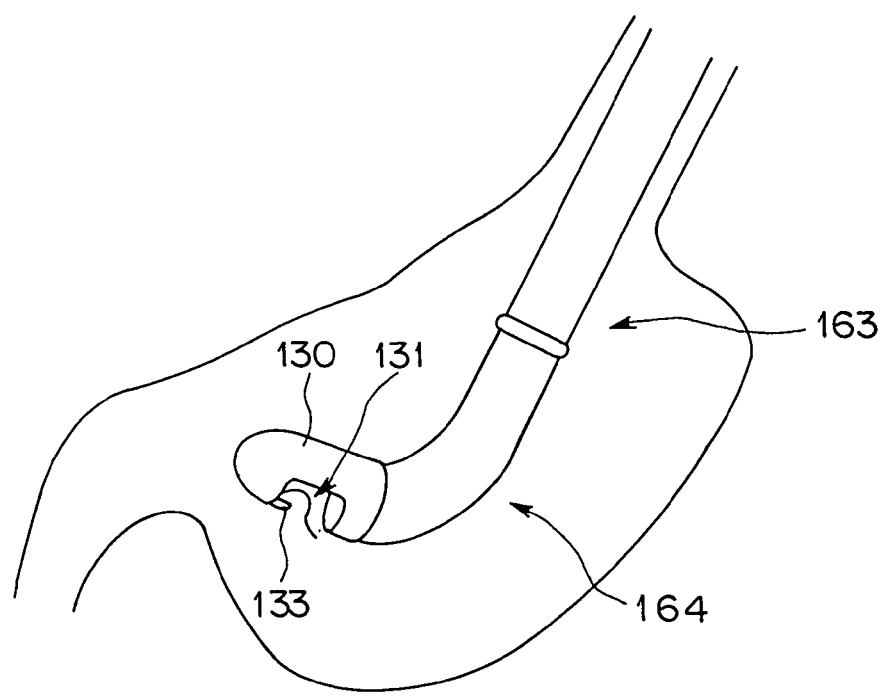
FIG. 32 is a diagram for explaining a state in which the distal-end hood is used in the stomach.

Referring to FIG. 31, the operating portion comprises the treatment tool lead-in portion, the bending operating knob, a lever 161 which advances and returns the hood drawing wire 128 or which is interlocked to an electromagnetic valve (not shown) arranged to the halfway portion of the air feed tube 160, and a rotating ring 162 which advances and returns the pricking needle 126. The lever 161 is rotated as shown by the arrow, thereby advancing and returning the hood portion 155 forming the distal-end hood 130 or the distal-end hood 154. The rotating ring 162 is rotated as shown by an arrow, thereby advancing and returning a wire member (not shown). Further, the pricking needle 126 is projected and returned from the hole 124 for inserting the pricking needle.

A description is given of the operation of the endoscope 120 in which the distal-end hood 130 is arranged to the distal-end rigid portion 121.

First, when the endoscope is inserted to the target portion in the body cavity such as the stomach, the claw-shaped hooks 133 is stored in the hook accommodating groove 135 in the state in which the distal-end hood 130 is drawn to the most proximal-end side. Thus, in the inserting operation, the hooking to the body wall of the claw-shaped hooks 133 is prevented.

In this state, while the bending knob of operating portion is operated on the hand side or the inserting portion is twisted, the bending portion 164 of the inserting portion 163 is bent, the distal-end rigid portion 121 is inserted near the target portion, and then the distal-end hood 130 is in contact with the body wall by the operation on the hand side.

Next, the operator operates the lever 161. Then, referring to FIG. 32, the distal-end hood 130 is opened and the hood concaved portion 131 appears. After that, the lever 161 is operated and the distal-end hood 130 is moved in the direction of the closing state. Then, in accordance with the operation, the body wall is hooked to the claw-shaped hooks 133 arranged to the inner wall surface 132 on the distal end side of the distal-end hood 130 and the claw-shaped hooks 133 are simultaneously moved. Thus, the body wall is drawn in the hood concaved portion 131 of the distal-end hood 130.

In this case, although not shown, the opening of the suction hole extended from the operating portion is arranged to the distal-end surface of the endoscope, the distal-end hood 130 is closed and simultaneously the suction operation is performed. Thus, the larger part of the body wall is drawn in the distal-end hood 130 with more securely.

Next, the distal-end hood 130 is further drawn to the hand side. Then, the organ in the body cavity drawn in the hood concaved portion 131 is pressed and is sandwiched between the inner wall surface 132 on the distal end side of the distal-end hood 130 and the distal-end surface 121a of the distal-end rigid portion 121.

Next, the rotating ring 162 is operated in the pressing and sandwiching state and the pricking needle 126 is projected from the hole 124 for inserting the pricking needle. In this case, since the body wall is pressed and is sandwiched between the inner wall surface 132 on the distal end side and the distal-end surface 121a, the pricking operation is certainly and stably performed without detaching the body wall.

The two T-bars 141 shown in FIG. 27A are stored in the through-hole of the pricking needle 126. After completing the pricking operation to the body wall of the pricking needle 126, referring to FIG. 27C, the pusher 145 is pressed in the distal end direction. Then, one T-bar 141 is projected from the through-hole of the pricking needle 126.

Figure 33A:
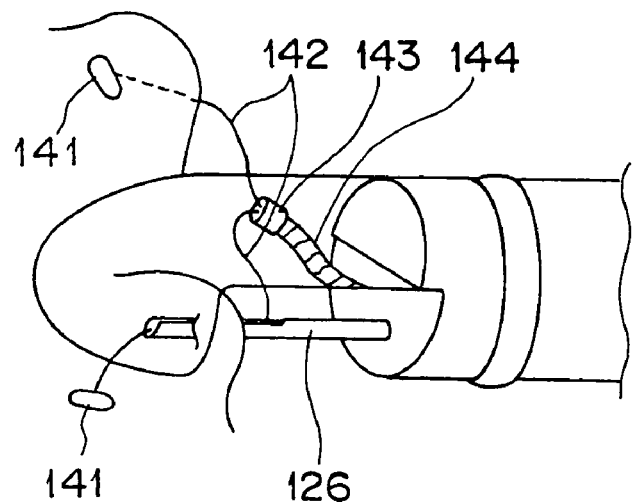
FIG. 33A is a diagram for explaining a state in which a second T-bar is projected.

After projecting the one T-bar 141, the distal-end rigid portion 121 is moved and another portion of the body wall is pressed and sandwiched in the above-mentioned procedure. The pricking operation is performed again and the other T-bar 141 is projected to the body wall as shown in FIG. 33A.

Figure 33B:
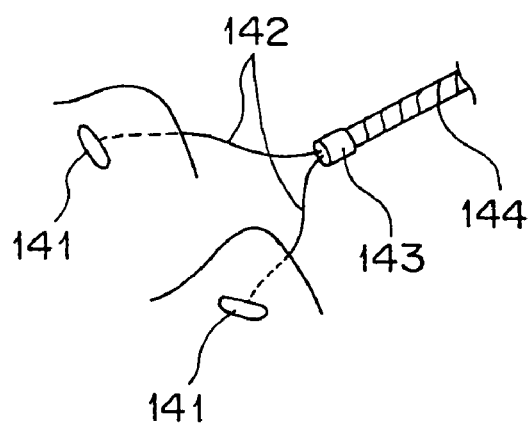
FIG. 33B is a diagram for explaining a state in which the interval between the T-bars is narrow and the T-bars are tightened.
Figure 33C:
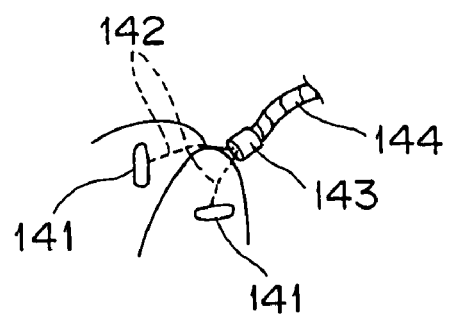
FIG. 33C is a diagram for explaining a state in which the two projected T-bars are close to each other.

After projecting the two T-bars 141, referring to FIG. 33B, the tightening tool 144 is tightened on the hand side, the interval between the T-bars 141 is narrowed, and the T-bars 141 are tightened. Then, referring to FIG. 33C, the T-bars 141 projected to two portions are close to each other and the suturing operation is performed in this state.

Depending on the portion for pricking and suturing operation, the distance between the two pricking portions is previously known. In this case, the length of the connecting thread 142 is adjusted in accordance with the distance between the two portions. Thus, the processing for tightening with the tightening tool 144 is omitted.

As mentioned above, the distal-end hood is arranged to advance and return to the distal-end rigid portion, and the claw-shaped hook is arranged to hook the body wall to the distal-end hood. Thus, the movement of the distal-end hood draws the body wall of the target portion in the hood concaved portion.

When the body wall is drawn in the hood concaved portion, the distal-end hood is moved to the hand side and the body wall is pressed and sandwiched. Thus, the pricking operation is performed in this state, thereby preventing the detachment of the body wall. The stable and certain pricking operation is performed.

Further, the pricking operation is certainly performed with the pricking needle. The suturing operation of the tissue in the body cavity is certainly performed. Therefore, the manual operation for stopping the bleeding by tightening the blood vessel of the bleeding portion or the manual operation for closing the pricking hole portion can be executed.

The lever and the rotating ring arranged to the operating portion advance and return the distal-end hood and the pricking needle. The operator operates the bending operating knob on the hand side, thereby performing the pricking operation. Thus, the operation for moving the position of the distal-end rigid portion is easy.

The similar manual operation is possible in the case of closing and opening the electromagnetic valve of the air feed tube 160 by operating the lever 161.

The fifth embodiment will be described with reference to FIGS. 34 to 39.

Figure 34:
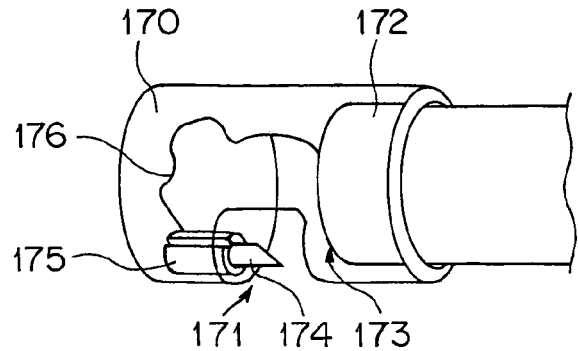
FIG. 34 is a diagram for explaining a state in which a distal-end hood having a pricking needle facing a distal-end surface in a hood concaved portion.

Referring to FIG. 34, a pricking needle 174 is projected, facing a distal-end surface 173 of a distal-end rigid portion 172, and is arranged in a hood concaved portion 171 of a distal-end hood 170 according to the fifth embodiment. The pricking needle 174 is detachably arranged to a needle base 175. A connecting thread 176 is connected to the proximal end portion of the pricking needle 174. An end portion of the connecting thread 176 is extended to the outside of the body via a thread path (not shown) arranged in the inserting portion of the endoscope. On the other hand, a needle receiving portion holds and fixes the pricking needle 174, as will be described later, is arranged to the distal-end surface of the distal-end rigid portion.

Figure 35:
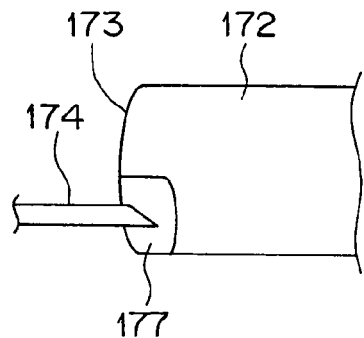
FIG. 35 is a diagram for explaining one example of the structure of a needle receiving portion.
Figure 36:
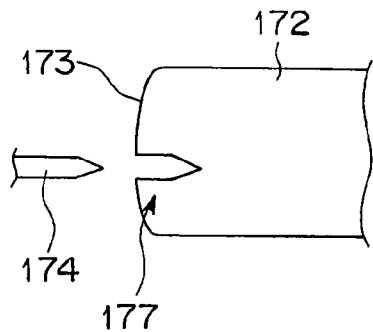
FIG. 36 is a diagram for explaining another example of the structure of the needle receiving portion.
Figure 37:
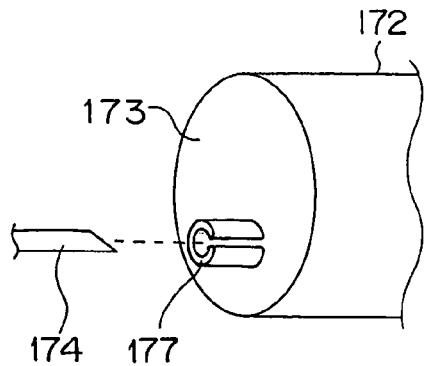
FIG. 37 is a diagram for explaining another example of the structure of the needle receiving portion.

The needle receiving portion 177 is structured as shown in FIGS. 35 to 37. Referring to FIG. 35, the needle receiving portion 177 contains a soft member such as rubber or spongy. The pricking needle 174 is pricked to the needle receiving portion 177 and then the pricking needle 174 is fixed in the soft member by the friction force of the soft member. Referring to FIG. 36, the needle receiving portion 177 has a taper-shaped hole portion corresponding to the needle tip of the pricking needle 174, and the pricking needle 174 is engaged and fixed to the taper-shaped hole portion. Referring to FIG. 37, the needle receiving portion 177 is a pipe-shaped sheath projected from the distal-end surface 173 of the distal-end rigid portion 172, and has a slit on the side surface of the pipe-shaped sheath to be elastically modified. The hole diameter of the pipe-shaped sheath is thinner than the outer diameter of the pricking needle 174. Therefore, the pricking needle 174 is pricked and is engaged and arranged in the pipe-shaped sheath, then, the pipe-shaped sheath is elastically modified, thereby fixing the pricking needle with the biasing force.

Here, a description is given of the operation of the pricking needle 174 arranged to the distal-end hood 170.

Figure 38A:
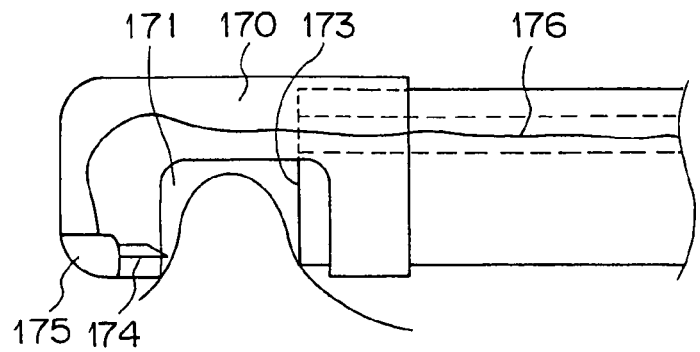
FIG. 38A is a diagram for explaining a state in which the body tissue is drawn into the hood concaved portion.
Figure 38B:
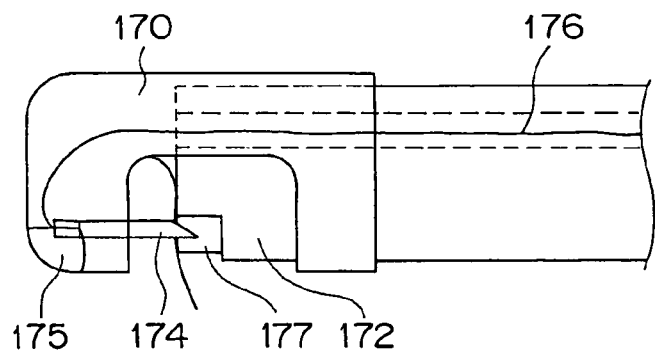
FIG. 38B is a diagram explaining a state in which the pricking needle is pricked in the body tissue drawn into the hood concaved portion and the tip of the pricking needle is fixed to the needle receiving portion.

Referring to FIG. 38A, the hood concaved portion 171 of the distal-end hood 170 is moved to the hand side from the position in the opening state, thereby pulling the body wall in the hood concaved portion 171. Next, referring to FIG. 38B, the distal-end hood 170 is moved back so as to sandwich the body tissue between the inner wall surface on the distal end side of the distal-end hood 170 and the distal end surface 173 of the distal-end rigid portion 172. At this time, the pricking needle 174 simultaneously pricks the body tissue. The hood concaved portion 131 is closed, then, the tip of the pricking needle 174 pricks the needle receiving portion 177, and the pricking needle 174 is fixed to the needle receiving portion 177.

Figure 38C:
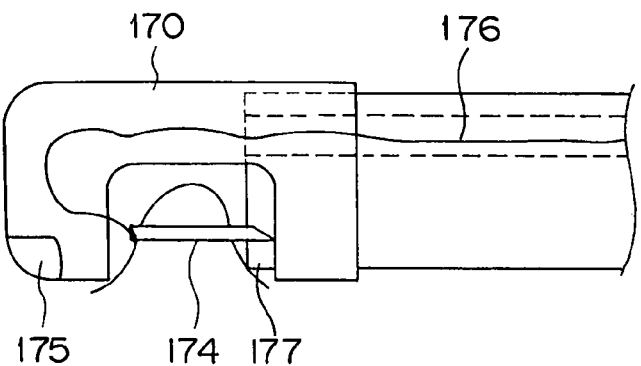
FIG. 38C is a diagram for explaining a state in which the pricking needle is detached from a needle base.
Figure 38D:
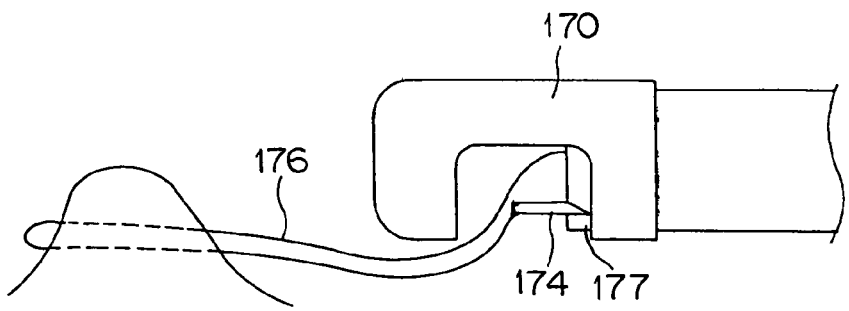
FIG. 38D is a diagram for explaining a state in which the endoscope is removed while the connecting thread remains in the body tissue.

In this state, referring to FIG. 38C, the distal-end hood 170 is opened again. Then, the needle tip of the pricking needle 174 is fixed to the needle receiving portion 177 and then the body tissue is detached from the needle base 175 of the pricking needle 174. Referring to FIG. 38D, the endoscope is removed from the body cavity, thereby pulling out the pricking needle 174 connected to the end portion of the connecting thread 176 together with the endoscope.

Figure 39:
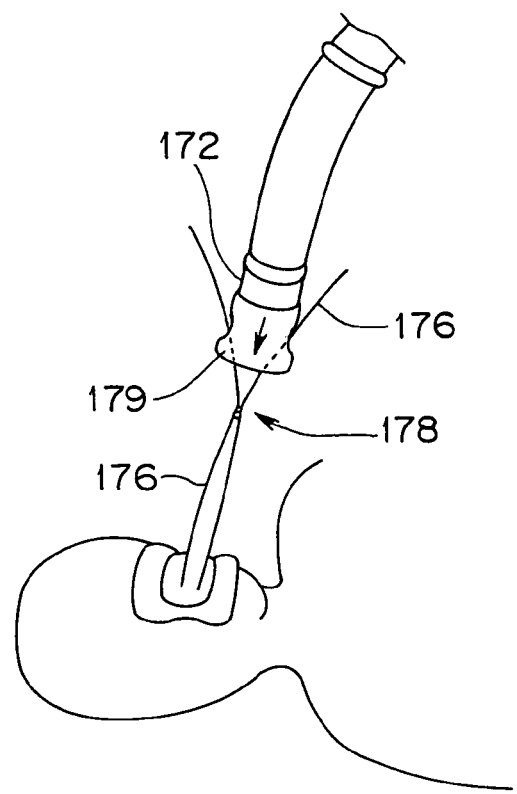
FIG. 39 is a diagram for explaining a state in which a knot pusher feeds a knot portion in the body cavity.

Referring to FIG. 39, a knot 178 is formed outside the body. A knot pusher 179 feeds the knot 178 into the body cavity. Thus, the body tissue is sutured.

The knot pusher 179 comprises a cap having a groove for stopping or inserting the connecting thread 176 to the distal-end rigid portion 172. Thus, only the connecting thread 176 enables the suturing operation of body cavity without another remaining.

As mentioned above, the pricking needle is arranged to be detachable from the distal-end hood. When the pricking needle is pricked to the distal-end rigid portion of the endoscope inserting portion, the needle receiving portion is arranged to hold and fix the pricking needle. Thus, the body wall is certainly sutured without deteriorating the operability.

Figure 40:
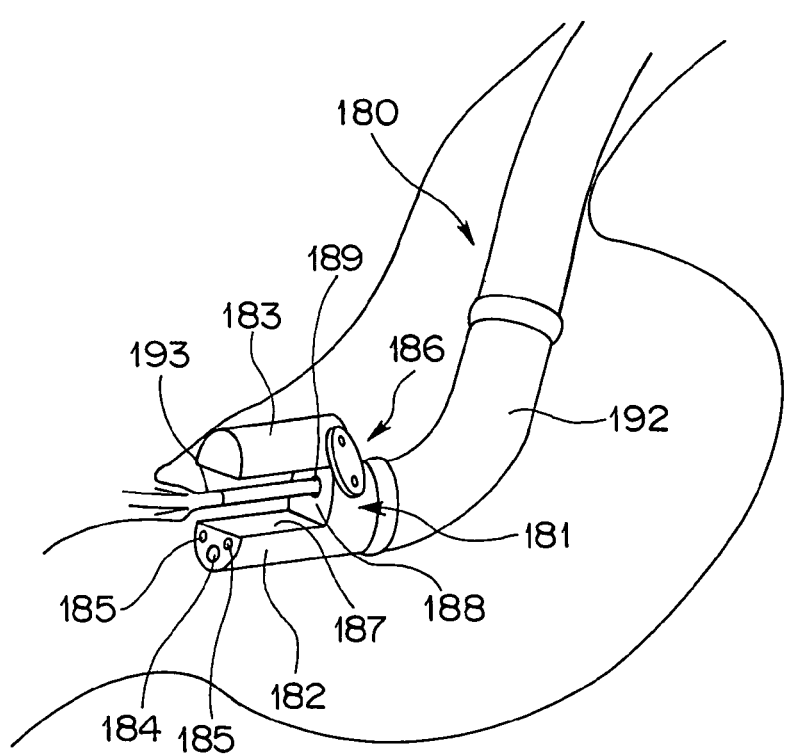
FIG. 40 is a diagram for explaining a distal-end rigid portion comprising a fixed portion and a movable portion.
Figure 41:
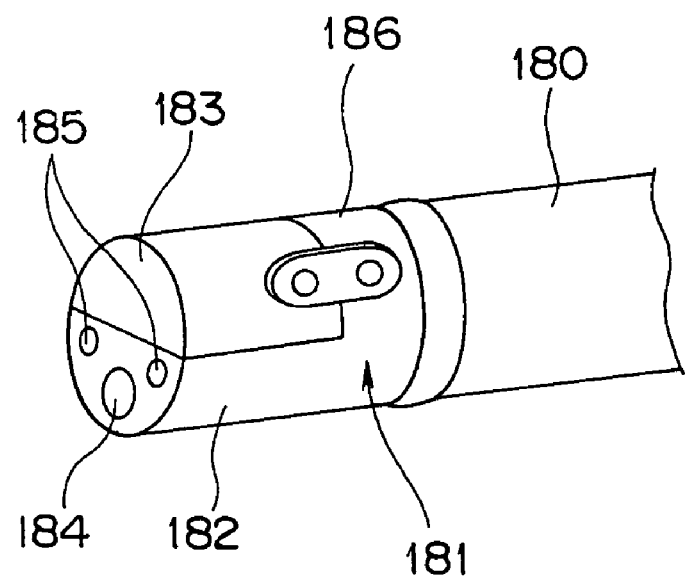
FIG. 41 is a diagram showing a distal-end rigid portion which is closed.
Figure 42:
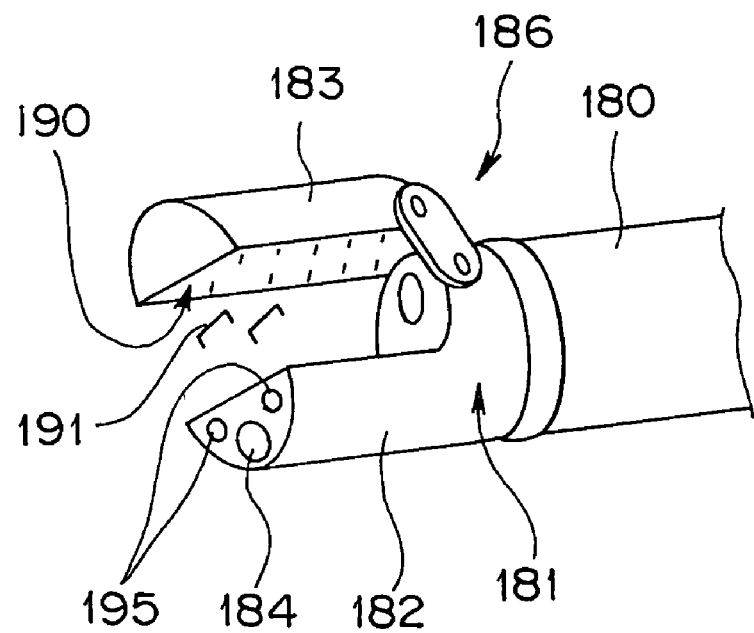
FIG. 42 is a diagram showing the distal-end rigid portion which is opened.

A description is given of the sixth embodiment with reference to FIGS. 40 to 42.

Referring to FIGS. 40 to 42, a distal-end rigid portion 181 forms an endoscope inserting portion 180 according to the sixth embodiment. The distal-end rigid portion 181 comprises a fixed portion 182 and a movable portion 183. An observing cover 184 and an illuminating cover 185 are arranged to the distal-end surface of the fixed portion 182.

The fixed portion 182 is structured as the distal-end rigid portion 181. The movable portion 183 is connected to the fixed portion 182 via a link mechanism 186. Thus, the movable portion 183 holds the parallel state with the fixed portion 182, and is gradually opened. The operator-operates a knob (not shown) arranged to the operating portion, thereby performing closing and opening operation of the movable portion 183.

Referring to FIG. 41, when the endoscope inserting portion 180 is inserted in the body cavity, the movable portion 183 and the fixed portion 182 are closed. By the operation on the hand side of the operator, the movable portion 183 is opened as shown in FIG. 40. Then, an inner plain surface 187 and a wall surface 188 of the fixed portion 182 are exposed, and a distal end opening 189 arranged to the wall surface 188 is exposed.

Various treatment tools are projected to the distal end opening 189. That is, the distal end opening 189 is a treatment tool guiding port. Only when the movable portion 183 is opened, the distal end opening 189 is opened between the movable portion 183 and the fixed portion 182.

Referring to FIG. 42, a plurality of grooves are arranged to an inner plain surface 190 on the side of the movable portion 183. Staplers 191 are arranged to the grooves. The staplers 191 are U-shaped, containing a metallic member. Both ends of the staplers 191 are sharply formed, and both needles are folded with predetermined amount of force. The staplers 191 are shot out to the outside from the movable portion 183 by operating an operating portion (not shown).

The staplers 191 are shot out and the movable portion 183 is closed to be close to the fixed portion 182. Thus, the staplers 191 are sandwiched between the movable portion 183 and the fixed portion 182. On then inner plain surface 187 of the fixed portion 182 comprising the plain surfaces, both the needles of the staplers 191 are pressed and are folded.

A description is given of the operation of the endoscope having the distal-end rigid portion having the fixed portion 182 and the movable portion 183.

A bending portion 192 of the endoscope inserting portion 180 is operated, and thus the distal-end rigid portion 181 is close to the target portion. The movable portion 183 is opened and grip forceps 193 are projected from the distal end opening 189. Thus, the body tissue is arranged between the movable portion 183 and the fixed portion 182. The body tissue is drawn between the movable portion 183 and the fixed portion 182 and simultaneously the staplers 191 are shot out. Then, the movable portion 183 is moved to be closed. The needles of the staplers 191 are pricked into the organ and then the needles are pressed and are folded. Thus, the body tissue is needle-stopped by the staplers 191.

According to the sixth embodiment, the movable portion 183 is moved in parallel with the fixed portion 182. Thus, the space necessary for the opening and closing operation may have an area in which the movable portion 183 is moved, in addition to the space for arranging the fixed portion 182. If the movable portion is arranged like a pivot to the fixed portion 182 and is opened/closed, the space is necessary for the rotation with the radius from the free end to the fixed end of an opening and closing member.

As mentioned above, the staplers are arranged to the movable portion which is closed and opened to the fixed portion in parallel therewith and thus the desired portion is easily ligated in the narrow organ such as the lumen in addition to the large organ.

The suturing function is included in the endoscope inserting portion having the bending portion. Thus, the bending portion is used, thereby easily arranging the staplers to the target portion and arranging the same in the desired direction. Consequently, the easy pricking and suturing operation are possible.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope for treatment suitable for treatment in a body cavity, comprising:
    an elongate flexible observing optical unit having at least an observing optical system; and
    a unit inserting tool having a unit inserting channel in which the observing optical unit is inserted and a treatment tool inserting channel in which a treatment tool is inserted,
    wherein the unit inserting channel of the unit inserting tool has a branching portion at which the unit inserting channel is branched into a first inserting channel and a second inserting channel, an observing window located in an opening at the end of the first inserting channel is provided at a surface of the distal end portion of the unit inserting channel, and an observing window located in an opening at the end of the second inserting channel is provided at a surface at a halfway portion of the unit inserting channel, and
    wherein the unit inserting tool comprises an optical unit lead-in port to lead in the observing optical unit and at least one treatment tool lead-in port in which the treatment tool is inserted at the proximal end portion thereof, and
    a treatment tool lead-out port communicated with the treatment tool inserting channel extended from the treatment tool lead-in port at at least one of the surface of the distal end portion of the unit inserting channel and the surface at the halfway portion of the unit inserting channel.

2. An endoscope for treatment according to claim 1, further comprising:
    a bending mechanism portion which is changed to a straight state or a bending state by the operation on the hand side at the distal end portion side of the observing optical unit.

3. An endoscope for treatment according to claim 1, wherein a bending proclivity portion is arranged at the distal end portion of the observing optical unit.

4. An endoscope for treatment according to claim 1, wherein a channel switching mechanism for selecting the inserting direction of the observing optical unit which is inserted in the unit inserting channel is arranged at the branching portion which branches the unit inserting channel, in which the observing optical unit is inserted, into an inserting channel in the direction of the observing window at the distal end portion and an inserting channel in the direction of the observing window at the halfway portion.

5. An endoscope for treatment tool according to claim 4, wherein the channel switching mechanism comprises:
- a rotating plate which is rotatably arranged;
- a biasing member which biases the rotating plate so as to cover an opening into a first unit inserting channel; and
- a drawing operating wire which moves the rotating plate by the drawing operation against biasing force of the biasing member.

6. An endoscope for treatment tool according to claim 1, wherein the unit inserting tool has a bending portion which is independently bent by the hand side operation at least either between the distal end portion and the halfway portion or on the rear side of the halfway portion.

7. An endoscope for treatment tool according to claim 1, wherein, when the unit inserting tool is in the straight state, at least either one of the optical axis of the observing widow provided at the surface of the distal end portion and the optical axis of the observing window provided at the surface at the halfway portion is in parallel with the longitudinal axial direction of the unit inserting tool.

8. An endoscope apparatus for treatment, comprising:
- an endoscope for treatment having first and second inserting portions, the second portion extending in a distal direction from a distal-most end of the first inserting portion and the second inserting portion having a diameter smaller than a diameter of the first inserting portion, the endoscope having first and second observing optical systems provided with first and second image pick-up devices provided at a first surface at the distal-most end of the first inserting portion and at a second surface provided on the second inserting portion, respectively;
- a video processor for processing electric signals photoelectrically converted by the image pick-up devices provided at the first and second surfaces into video signals;
- a monitor which receives the video signals processed by the video processor and displays observation images;
- a change-over device which transmits the electric signals photoelectrically converted by the image pick-up devices provided at the first and second surfaces to the video processor to display the observation images on a screen of the monitor;
- first and second treatment tool lead-out ports provided at the first and second surfaces, respectively and communicated with a treatment tool inserting channel; and
- first and second treatment tool lead-in ports provided at an operation portion arranged at the proximal end of the first inserting portion and communicated with the treatment tool inserting channel wherein the second observing optical system and the second treatment tool lead-out port at the second surface are provided so as to be capable of being directed to the first treatment tool lead-out port at the first surface.

9. An endoscope apparatus for treatment according to claim 8, wherein the operation portion of the endoscope has change-over means which switches and displays, on the screen of the monitor, the observation image which is captured by the first image pick-up device at the first surface or the observation image which is captured by the second image pick-up device at the second surface.

10. An endoscope apparatus for treatment, comprising:
- an endoscope for treatment having first and second inserting portions, the second portion extending in a distal direction from a distal-most end of the first inserting portion and the second inserting portion having a diameter smaller than a diameter of the first inserting portion, the endoscope having first and second observing optical systems provided with first and second image pick-up devices provided at a first surface at the distal-most end of the first inserting portion and at a second surface provided on the second inserting portion, respectively;
- a first video processor for processing an electric signal photoelectrically converted by the first image pick-up device provided at the first surface into a video signal;
- a second video processor for processing an electric signal photoelectrically converted by the second image pick-up device provided at the second surface into a video signal;
- a first monitor which receives the video signal processed by the first video processor and displays an observation image;
- a second monitor which receives the video signal processed by the second video processor and displays an observation image;
- first and second treatment tool lead-out ports provided at the first surface and the second surface, respectively and communicated with a treatment tool inserting channel; and
- first and second treatment tool lead-in ports provided at an operation portion arranged at the proximal end of the inserting portion and communicated with the treatment tool inserting channel;

wherein the second observing optical system and the second treatment tool lead-out port at the second surface are provided so as to be capable of being directed to the first treatment tool lead-out port at the first surface.

* * * * *